United States Patent
Gerashchenko et al.

(10) Patent No.: US 12,194,147 B2
(45) Date of Patent: Jan. 14, 2025

(54) HYDROPHILIC/HYDROPHOBIC PHARMACEUTICAL COMPOSITION AND METHOD OF ITS PRODUCTION AND USE

(71) Applicant: Pathelen Health Care AG, Rorschach (CH)

(72) Inventors: Igor Gerashchenko, Kyiv (UA); Oleksii Chepliaka, Vinnytsia (UA); Andreas Tausch, Rorschach (CH)

(73) Assignee: PATHELEN HEALTH CARE AG, Rorschach (CH)

( * ) Notice: Subject to any disclaimer, the term of this patent is extended or adjusted under 35 U.S.C. 154(b) by 376 days.

(21) Appl. No.: 16/965,077

(22) PCT Filed: Jan. 28, 2019

(86) PCT No.: PCT/EP2019/052021
§ 371 (c)(1),
(2) Date: Jul. 27, 2020

(87) PCT Pub. No.: WO2019/145546
PCT Pub. Date: Aug. 1, 2019

(65) Prior Publication Data
US 2021/0106531 A1  Apr. 15, 2021

(30) Foreign Application Priority Data
Jan. 29, 2018 (EP) ..................... 18000067

(51) Int. Cl.
| A61K 45/06 | (2006.01) |
| A61K 9/00 | (2006.01) |
| A61K 9/14 | (2006.01) |
| A61K 33/00 | (2006.01) |
| A61L 15/18 | (2006.01) |
| A61L 15/44 | (2006.01) |
| A61L 15/60 | (2006.01) |

(52) U.S. Cl.
CPC ............ *A61K 9/143* (2013.01); *A61K 9/0014* (2013.01); *A61K 9/145* (2013.01); *A61K 33/00* (2013.01); *A61K 45/06* (2013.01); *A61L 15/18* (2013.01); *A61L 15/44* (2013.01); *A61L 15/60* (2013.01); *A61L 2300/404* (2013.01)

(58) Field of Classification Search
CPC ...... A61K 9/143; A61K 9/0014; A61K 9/145; A61K 33/00; A61K 45/06; A61L 15/18; A61L 15/44; A61L 15/60; A61L 2300/404
See application file for complete search history.

(56) References Cited

U.S. PATENT DOCUMENTS

| 8,466,228 | B2 | 6/2013 | Smith et al. | |
| 2004/0092415 | A1 | 5/2004 | Focht et al. | |
| 2006/0278847 | A1* | 12/2006 | Walzer | A61L 15/46 |
| | | | | 252/186.23 |
| 2010/0240532 | A1 | 9/2010 | Tolcheyev et al. | |
| 2010/0291062 | A1 | 11/2010 | Golub et al. | |
| 2013/0058880 | A1 | 3/2013 | Dong | |
| 2016/0206709 | A1 | 7/2016 | Golub et al. | |
| 2016/0271294 | A1* | 9/2016 | Gerashchenko | C08G 77/06 |

FOREIGN PATENT DOCUMENTS

| CN | 101772356 | A | | 7/2010 | |
| CN | 102811724 | A | | 12/2012 | |
| EP | 0162026 | A2 | | 11/1985 | |
| EP | 1721662 | A1 | | 11/2006 | |
| EP | 2277559 | A1 | | 1/2011 | |
| EP | 2476420 | A1 | | 7/2012 | |
| JP | S60210256 | A | | 10/1985 | |
| JP | 2001335410 | A | * | 12/2001 | |
| JP | 2006506388 | | * | 10/2003 | |
| JP | 201521111 | A | | 2/2015 | |
| JP | 2016535790 | A | | 11/2016 | |
| JP | 2017114771 | | * | 6/2017 | |
| KR | 950013505 | A | * | 6/1995 | |
| UA | 32088 | C2 | | 12/2000 | |
| UA | 82774 | C2 | | 5/2008 | |
| UA | 33629 | U | | 7/2008 | |
| WO | 2008051513 | A2 | | 5/2008 | |
| WO | 2010079209 | A2 | | 7/2010 | |
| WO | WO-2015067603 | A1 | * | 5/2015 | .......... A61K 31/167 |
| WO | 2016071405 | A2 | | 5/2016 | |

OTHER PUBLICATIONS

"Silica, Colloidal Hydrated," European Pharm. 6.0, 1 page (2008).
(Continued)

*Primary Examiner* — Ali Soroush
(74) *Attorney, Agent, or Firm* — Panitch Schwarze Belisario & Nadel LLP

(57) ABSTRACT

A method of producing a composition in powder form involves the following steps (a) to (c):
(a) providing highly dispersed silica particles, hydrophobic silica particles, and a cationic surfactant;
(b) forming primary hydrophobic silica particles carrying the cationic surfactant on their surface and/or agglomerates of these primary particles; and
(c) mixing the highly dispersed silica particles with the product obtained in step (b), thereby obtaining the composition in powder form; and a composition in powder form obtainable by the method.

22 Claims, No Drawings

(56) References Cited

OTHER PUBLICATIONS

Azuma et al., "Immunological Modulation by Lidocaine-Epinephrine and Prilocaine-Felypressin on the Functions Related to Natural Immunity in Neutrophils and Macrophages," Current Drug Targets, Immune, Endocrine and Metabolic Disorders, vol. 4, No. 1, 1 pg. (2004) (Abstract Only).
Baksa, "Selection of Wound Dressings," J. Orvosi Hetilap, vol. 141, No. 47, pp. 2549-2554 (2000) (English Abstract).
Blitz, "Surface Chemistry in Biomedical and Environmental Science," NATO Science Series, vol. 228, 458 pages (2006).
Bradley et al., "Systematic Reviews of Wound Care Management: (2) Dressings and Topical Agents Used in the Healing of Chronic Wounds," Healthcare Technology Assessment, vol. 3, No. 17, Pt. 2, 143 pages (1999).
Chepliaka, "Complex Treatment of Anorectal Abscess Patients," Dissertation of PhD Vinnytsya, 3 pgs. (2006) (English Summary).
Chuiko et al., "Application Efficiency of Complex Preparations Based on Nanodisperse Silica in Medical Practice," Nanomaterials and Supramolecular Structures, Springer Science, pp. 53-62 (Jan. 1, 2009).
Chuiko et al., "Medical Aspects of Application of Highly Disperse Amorphous Silica," Surface Chemistry in Biomedical and Environmental Science, Ed. Biltz et al., pp. 191-204 (2006).
Cooney, D., "Activated Charcoal in Medical Application," CRC Press, 602 pages (1995).
Council of Europe, "BACITRACIN" European Pharmacopoeia, vol. 5., Suppl. 5.1 and 5.2, pp. 1245-1247 (2005).
Donaldson et al., "Ciprofloxacin in General Practice," BMJ (Clinical Research Ed.), vol. 308, pP. 1437 (May 1994).
Fleck, "Palliative Dilemmas: Wound Odour," Wound Care Canada, vol. 4, No. 3, pp. 10-13 (2006).
Furr et al., "Antibacterial Activity of Actisorb Plus, Actisorb and Silver Nitrate," Journ. of Hospital Infection, vol. 27, No. 3, pp. 201-208 (1994).
Goryunov et al., "Purulent Surgery: Atlas," BINOM. Laboratory of Science, pp. 504-506 (2004) (English Abstract).
Huang et al., "Risk of Methicillin-Resistant *Staphylococcus aureus* Infection after Previous Infection or Colonization," Clinical Infectious Diseases, vol. 2003, No. 36, pp. 281-285 (Jan. 2003).

Int'l Search Report issued Jan. 16, 2015 in Int'l Application No. PCT/EP2014/073698.
Kaye et al., "The Deadly Toll of Invasive Methicillin-Resistant *Staphylococcus aureus* Infection in Community Hospitals," Clinical Infectious Diseases, vol. 46, pp. 1568-1577 (Apr. 3, 2008).
Lemaire et al., "Activity of Fusidic Acid Against Extracellular and Intracellular *Staphylococcus aureus*: Influence of pH and Comparison with Linezolid and Clindamycin," Clinical Infectious Diseases, vol. 52, Suppl. 7, pp. S493-S503 (2011).
Moore, "Silicon Dioxide," Pharmacopeial Forum, vol. 31, No. 4, pp. 1229 (2007).
Office Action issued Jan. 30, 2018 in U.S. Appl. No. 15/034,615, by Gerashchenko.
Office Action issued Jun. 20, 2017 in U.S. Appl. No. 15/034,615, by Gerashchenko.
Office Action issued Jun. 21, 2018 in CN Application No. 201480072167.7.
Rutkovskii et al., "Rationale of the Application of Sorption-Lymphatic Techniques in the Treatment of Anorectal Abscess," Lecture on IV Republican Scientific Practical Conference with Participation of International Proctologists "Functional and Inflectional Diseases of Large Intestine: Surgical and Therapeutic Aspects. New in Coloproctology," pp. 78-79 (2001) (English Translation).
Skorkowska-Telichowska et al., "The Local Treatment and Available Dressings Designed for Chronic Wounds," J. Am. Acad. Dermatol., vol. 68, No. 4, e1-e10 (2011).
Sutherland et al., "Antibacterial Activity of Mupirocin (Pseudomonic Acid), a New Antibiotic for Topical Use," Antimicrobial Agents and Chemo., vol. 27, No. 4, pp. 495-498 (Apr. 1985).
Woo et al., "Local Wound Care for Malignant and Palliative Wounds," Advances in Skin & Wound Care: Journ. for Prevention and Healing, vol. 23, No. 9, pp. 417-428 (Sep. 2010).
Int'l Search Report and Written Opinion issued Apr. 4, 2019 in Int'l Application No. PCT/EP2019/052021.
Office Action issued Oct. 25, 2022 in JP Application No. 2020-562846.
Office Action issued Jul. 19, 2023 in JP Application No. 2020-562846 (English translation).
Gun'ko et al., "Comparative characterization of polymethylsiloxane hydrogel and silylated fumed silica and silica gel," Journal of Colloid and Interface Science, vol. 308, pp. 142-156 (2007).

\* cited by examiner

HYDROPHILIC/HYDROPHOBIC PHARMACEUTICAL COMPOSITION AND METHOD OF ITS PRODUCTION AND USE

CROSS-REFERENCE TO RELATED APPLICATIONS

This application is a Section 371 of International Application No. PCT/EP2019/052021, filed Jan. 28, 2019, which was published in the English language on Aug. 1, 2019 under International Publication No. WO 2019/145546 A1, which claims priority under 35 U.S.C. § 119 (b) to European Application No. 18000067.1, filed on Jan. 29, 2018, the disclosures of which are incorporated herein by reference in their entireties.

TECHNICAL FIELD

The invention relates to new compositions based on highly dispersed silica and hydrophobic silica that have wide range sorptive, high anti-inflammatory and wound-healing abilities that can be used in different fields of practical medicine for the treatment of diseases which are caused by pathogenic microorganisms, in particular, purulent wounds.

Healing of infected ulcers and wounds, particularly in old men, is a serious problem in modern surgery. Clinical practice shows that the treatment of purulo-inflammatory diseases and purulent wounds by using modern antimicrobial agents only does not always lead to the desired result. Misuse of antibiotics contributes to the emergence of resistant (hospital) strains of pathogenic microorganisms, including methicillin-resistant *Staphylococcus aureus* (MRSA), which is a serious challenge for modern medicine in general [Huang S S, Platt R., "Risk of methicillin-resistant *Staphylococcus aureus* infection after previous infection or colonization", Clin. Infect. Dis., 2003, vol. 36, p. 281-285; Kaye K, Anderson D, Choi Y, et al., "The deadly toll of invasive methicillin-resistant *Staphylococcus aureus* infection in community hospitals", Clin. Infect. Dis., 2008, vol. 46, p. 1568-1577].

The intensity of the regeneration process and healing of infected ulcers and wounds depends largely on the speed at which they are cleared from the pus and necrotic tissues. For this purpose applique sorption, i.e., a method of wound healing in which a sorbent in powder form is applied to the wound as a powder dressing, also known as sorption-applique treatment, can be used. Applique sorption is a kind of sorption detoxification which accelerates wound healing and restores the integrity of the skin and mucous membranes by the removal of microbial cells, bacterial toxins and toxic metabolites of wound fluid and wound cavities in direct contact with the surface of the sorptive preparation [Sorbents and Their Clinical Applications (Ed. C. Giordano), New-York-London, Academic Press, 1980; Cooney, D. O., "Activated charcoal in medical applications.", Marcel Dekker, Inc., New York-Basel-Hong Kong, 1995]. An important therapeutic factor in the first phase of wound healing is also seen in the dehydration, i.e., absorption of fluid from the wound cavity and perifocal tissues.

BACKGROUND ART

As sorption preparations for topical treatment of wounds materials based on activated carbon, various swelling polymers of synthetic and natural origin and silicon sorbents, such as sorbents derived from silica and silicone compounds, have been proposed.

Among the carbon preparations for wound healing Actisorb Plus (Johnson & Johnson) is particularly well-known, which is an activated carbon fiber coated with colloidal silver. Actisorb Plus has a nonspecific antimicrobial effect due to silver and the carbon sorbent can absorb pathogenic metabolites that accumulate in the wound contents. The preparation is used primarily for the healing of superficial wounds and skin defects, such as venous ulcers [Furr J. R., Russell A. D., Turner T. D., Andrews A., "Antibacterial activity of Actisorb Plus, Actisorb and silver nitrate", J. Hosp. Infect., 1994, vol. 27(3), p. 201-208]. However, activated carbon having nanometer pore size cannot absorb large protein molecules, which include bacterial toxins and tissue degradation products.

Methods of sorption-applique treatment of purulent wounds by complex sorbent SUMS-1 (Activated charcoal+ Aluminium oxide) with immobilized metronidazole [Rutkovskiy E. A., Shtofin S. G., Lubarskiy M. S., Yakushenko V. K., "Grounding for application of sorption lymphogenous methods in healing of anorectal abscess", Lecture on IV Republican scientific practical Conference with participation of international proctologists "Functional and inflectional diseases of large intestine: surgical and therapeutic aspects. New in coloproctology" (6-7 Sep. 2001)—Minsk— 2001, p. 78-79] or enzymes (nigedase and hyaluronidase) have been proposed. Due to their pronounced porous structure activated carbon sorbents absorb substances of low and medium molecular weight. Metronidazole exhibits a high sensitivity towards anaerobic microflora, which is usually seen in anorectal abscesses. However, SUMS-1 has limited sorption capacity, low rates of water absorption and pathogenic proteins absorption due to its structure, so that it does not have anti-inflammatory properties. The duration of the nigedase and hyaluronidase action for a surface sorption-applicative detoxification in the first phase of wound healing is small (less than 16 hours), resulting in shortened fibrinolysis and necrolytic effects that reduce the effectiveness of the therapy and increase the duration of treatment [Lubarskiy M. S., Letyagin A. Y., Gabitov V. H., Semko V. V., Povazhenko A. A., "Sorption mineral carbon preparations in purulent-septic surgery", Russian Academy of Medical Sciences. Institute of Clinical and Experimental lymphology— Bishkek, Novosibirsk, St. Petersburg, 1994].

The disadvantage of carbon adsorbents if applied to wounds is that two to three hours after application onto a wound, they start forming a crust that prevents the outflow from the wound, and the adsorption process is greatly reduced. Part of the granules is introduced into the tissue and cannot be removed. The surface of the granules is coated with fragments of cells and protein molecules, which also reduces their adsorptive activity [Alimov M. M., Experience in application carbon sorbent in treatment complicated soft tissue wounds/Alimov M. M., Bahtiyarov O. R., Batyrov D. Sh. Sorption methods of detoxification and immune correction in Surgery: Collection of treatises.—Tashkent, 1984, p. 173-174].

Wound dressings are designed to keep the wound clean and free from contamination and also to promote wound healing, particularly in chronic wounds where there may be significant tissue loss, e.g.: hydrocolloid dressings, hydrogels, alginate dressings and others [Skorkowska-Telichowska K., Czemplik M., Kulma A., Szopa J., "The local treatment and available dressings designed for chronic wounds", J. Amer. Acad. Dermatol., 2013, vol. 68(4), p. 117-126].

<<Gelevin>> is a basis of draining sorbents with an active mechanism of sorption and comprises a polyvinyl alcohol crosslinked with glutaraldehyde. The polymer has a structure that creates an irreversible sorption capacity for purulent wounds of 14-16 g/g. To reduce the multi pathogenetic effects on the purulent wound, immobilized preparations comprising bioactive draining sorbents that provide a chemotherapeutic wound cleansing (Diotevin, Anilodiotevin) are promising. They create conditions for prolonged release of the wound medications, such as antibiotics, antiseptics, proteolytic enzymes, local anesthetics. When these are applied to richly exuding wounds and brought into contact with the wound, they discharge biologically active sorbents which swell and become a coarse, easily removable gel. Release of the preparations occurs within one day and about 60% of the administered preparations are absorbed into the wound during the first hour. Antimicrobial agents such as Dioxidine can provide suppression of gram positive, gram negative and anaerobic microflora in the wound. Proteolytic enzymes (collagenase, terrylitine) contribute to the lysis of necrotic tissue. However, if the swollen sorbent granules are not carefully removed from the wounds having complex structure, with deep pockets and cavities, there are complications in applicative sorption therapy. Closure of the wound edges and encapsulation of large amounts of sorbent granules which represent a foreign body can lead to a recurrence of the purulent process or the formation of a fistula [Goryunov S. V., Romashov D. V., Butivshchenko, I. A.; under redaction of PhD Abramov M., "Purulent surgery: Atlas", BINOM. Laboratory of science, 2004, p. 504-506].

Also among sorbents the xerogel of methylsilicic acid-polymethylsiloxane is known that provides local wound detoxification due to active sorption of pathogens and low and middle molecular metabolites. Wound exudate fluid is "drained" through a capillary net of the powdered sorbent and organic substances are absorbed into its granules. By raising the pH of the wound it also potentiates the action of a specific antibiotic. Polymethylsiloxane can be used for the applique sorption with or without antibiotics immobilized on its surface. Exemplary preparations are Imosgent and Gentaxan in which the polymethylsiloxane surface is modified by gentamicin [Znamenskiy V. A., Vozianov A. F., Vozianova Zh. M. et al., Application of therapeutic preventive preparation produced on the silica based sorbents. Methodological recommendations, Kiev, 1994, p. 14.]. However, in the case of hydrophobic materials, the exudate is not absorbed and spreads rapidly under the bandage which promotes skin maceration and activation of the inflammatory process in the wound [Baksa J., "Selection of wound dressings", J. Orvisi Hetilap., 2000, vol. 141 (47), p. 2549-2554].

Hydrophilic highly dispersed silica (HDS) can be used in the first phase of wound healing. Its detoxifying action is due to the ability to absorb pathogenic protein substances (up to 800 mg/g), including microbial enzymes, endo- and exotoxins and microorganisms. The surface of the silica is covered with hydroxyl groups that can bind water molecules, so it produces a pronounced dehydrating effect on the tissue that is essential for the removal of edema as part of the inflammatory process. However, silica, due to lack of hydrophobic groups on its surface, does not absorb lipophilic and hydrophobic toxic metabolites. In some cases pure HDS has an excess dehydrating ability that causes non-desirable over-drying of tissues. HDS does not show direct antimicrobial action, however, it was found that the sensitivity of pathogenic organisms to antibiotics is increased in the presence of HDS [Blitz J. P. and Gun'ko V. M. (eds.), Surface Chemistry in Biomedical and Environmental Science, Springer, 2006, p. 191-204].

Noteworthy is a combination of hydrophilic and hydrophobic sorbents, providing sorption of a wide range of substances and pathogenic microorganisms in wounds. Through a combination of hydrophilic and hydrophobic sorbents these products can provide clean wounds through a selective sorption and managed draining effect.

The composite wound healing preparation "Flotoxan" and "Metroxan" which include highly dispersed silica and polymethylsiloxane (PMS) in a mixture with a surface-active substance such as ethonium [Ukrainian patents UA 32088 A, Wound healing preparation "Flotoxan" and way of its preparation, Shevchenko Y. M., Gerashchenko I. I., and Vil'tsanyuk O. A.; and UA 33629 A, Preparation for wound healing, Gerashchenko, I. I., Cheplyaka, O. M., Vil'tsanyuk, O. A., Burkovskiy M. I., and Zheliba M. D]. These preparations have a managed dehydrating effect which depends on the ratio "silica/PMS" and sufficient antimicrobial activity, the ability to absorb and to retain proteins, bacteria and their toxins, metabolites of middle molecular weight, whereby the resorption of the mentioned substances through the wound surface is prevented. Also, due to activation of protease activity by the preparation the content of the wound shows proteolytic properties although the preparation does not contain a component with antimicrobial activity against anaerobic microorganisms.

SUMMARY OF THE INVENTION

The aim of the invention is to eliminate the aforementioned shortcomings by creating a universal hydrophilic-hydrophobic composition having a sorptive and detoxifying effect for the treatment of purulent wounds and other purulo-inflammatory diseases such as chronic purulo-granulomatous inflammation, and purulo-necrotic inflammation. The composition according to this invention may be varied, depending on the phase of wound healing. This may be achieved by varying the dehydrating ability, adding compounds having a wide range of antimicrobial activity, e.g. against aerobic and anaerobic microorganisms. Moreover, additional compounds may be added which exhibit necrolytic effects on non-vital tissues, enhance the regenerative effect on the young tissue and/or provide a local anesthetic effect. By using the composition according to the present invention, a more effective treatment of wounds of different nature in various stages of wound healing may be achieved, which include: exudating wounds, chronic pressure ulcers, venous leg ulcers, diabetic/neuropathic ulcers, fungating, cancerous or malignant lesions and wounds with necrotic tissue.

Thus, the present invention provides in a first aspect a method of producing a composition in powder form comprising the following steps (a) to (c):
  (a) providing highly dispersed silica particles, hydrophobic silica particles, and a cationic surfactant;
  (b) forming primary hydrophobic silica particles carrying the cationic surfactant on their surface and/or agglomerates of these primary particles; and
  (c) mixing the highly dispersed silica particles with the product obtained in step (b), thereby obtaining the composition in powder form.

In a second aspect, the present invention provides a composition in powder form comprising highly dispersed silica, hydrophobic silica and a cationic surfactant.

The present invention also provides a pharmaceutical preparation which comprises the composition in powder form according to the second aspect of the present invention.

The present invention provides in a third aspect a method of producing a composition in powder form comprising the following steps:
(a) providing hydrophobic silica particles and a cationic surfactant; and
(b) forming primary hydrophobic silica particles carrying the cationic surfactant on their surface and/or in agglomerates of these primary particles,
thereby obtaining the composition in powder form.

In a fourth aspect the present invention provides a composition in powder form obtainable by the method according to the third aspect.

DETAILED DESCRIPTION

Thus, the present invention provides in a first aspect a method of producing a composition in powder form comprising the following steps (a) to (c):
(a) providing highly dispersed silica particles, hydrophobic silica particles, and a cationic surfactant;
(b) forming primary hydrophobic silica particles carrying the cationic surfactant on their surface and/or agglomerates of these primary particles; and
(c) mixing the highly dispersed silica particles with the product obtained in step (b), thereby obtaining the composition in powder form.

In the method of the first aspect of the present invention, the composition obtainable from the method preferably comprises:
21.0 to 75.0 wt. % of the highly dispersed silica,
16.0 to 70.0 wt. % of the hydrophobic silica, and
0.1 to 4.0 wt. % of the cationic surfactant,
based on the total weight of the composition.

When in the present application reference is made to the content of the composition obtainable from a method, it is understood that the respective components should be provided in the respective amounts at the beginning of the method and should be employed in the steps recited in the method, if not stated otherwise. Specifically, in the above embodiment, the method of the first aspect comprises the following steps (a) to (c):
(a) providing highly dispersed silica particles in an amount 21.0 to 75.0 wt. %, hydrophobic silica particles in an amount 16.0 to 70.0 wt. %, and a cationic surfactant in an amount 0.1 to 4.0 wt. %, based on the total weight of the composition;
(b) forming primary hydrophobic silica particles carrying the cationic surfactant on their surface and/or agglomerates of these primary particles; and
(c) mixing the highly dispersed silica particles with the product obtained in step (b), thereby obtaining the composition in powder form.

In the method of the first aspect of the present invention, the composition obtainable from the method more preferably comprises:
21.0 to 75.0 wt. % of the highly dispersed silica,
16.0 to 70.0 wt. % of the hydrophobic silica, and
0.05 to 4.0 wt. % of the cationic surfactant,
based on the total weight of the composition.

Even more preferably, the composition obtainable from the method of the first aspect of the present invention comprises:
35.0 to 70.0 wt. % of the highly dispersed silica,
20.0 to 45.0 wt. % of the hydrophobic silica, and
0.05 to 2.0 wt. % of the cationic surfactant,
based on the total weight of the composition.

Most preferably, the composition obtainable from the method of the first aspect of the present invention comprises:
35.0 to 70.0 wt. % of the highly dispersed silica,
20.0 to 45.0 wt. % of the hydrophobic silica, and
0.8 to 2.0 wt. % of the cationic surfactant,
based on the total weight of the composition.

With respect to the ratio of cationic surfactant and hydrophobic silica, the composition obtainable from the method of the first aspect of the present invention preferably comprises:
90.0 to 99.9 wt. % of the hydrophobic silica, and
0.1 to 10 wt. % of the cationic surfactant,
based on the total weight of hydrophobic silica and cationic surfactant.

More preferably, the composition obtainable from the method of the first aspect of the present invention preferably comprises:
90.0 to 99.8 wt. % of the hydrophobic silica, and
0.2 to 10 wt. % of the cationic surfactant,
based on the total weight of hydrophobic silica and cationic surfactant.

Even more preferably, the composition obtainable from the method of the first aspect of the present invention preferably comprises:
95.0 to 99.0 wt. % of the hydrophobic silica, and
0.5 to 5.0 wt. % of the cationic surfactant,
based on the total weight of hydrophobic silica and cationic surfactant.

It is further preferred, that the composition obtainable from the method of the first aspect of the present invention as described above further comprises at least one additional agent selected from the group consisting of antimicrobial substances, substances with tissue growth activity, lidocaine, phenothiazine derivatives, proteolytic enzymes, and combinations thereof.

More preferably, the composition obtainable from the method of the first aspect comprises at least one of the following additional agents (in addition to the highly dispersed silica particles, the hydrophobic silica particles, and the cationic surfactant):
0.5 to 10.0 wt. % of at least one antimicrobial substance,
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

Even more preferably, the composition obtainable from the method of the first aspect comprises:
21.0 to 75.0 wt. % of the highly dispersed silica,
16.0 to 70.0 wt. % of the hydrophobic silica, and
0.05 to 4.0 wt. % (preferably 0.1 to 4.0 wt. %) of the cationic surfactant; and
at least one of the following additional agents:
0.5 to 10.0 wt. % of an antimicrobial substance,
0.01 to 10.0 wt. % of at least one substance with tissue growth activity,
0.01 to 5.0 wt. % lidocaine,
0.01 to 5.0 wt. % of at least one phenothiazine derivative, and
0.01 to 3.0 wt. % of at least one proteolytic enzyme,
based on the total weight of the composition.

Most preferably, the composition obtainable from the method of the first aspect comprises:
35.0 to 70.0 wt. % of the highly dispersed silica,
20.0 to 45.0 wt. % of the hydrophobic silica, and 0.05 to 2.0 wt. % (preferably 0.8 to 2.0 wt. %) of the cationic surfactant; and at least one of the following additional agents:

0.5 to 10.0 wt. % of an antimicrobial substance, 0.01 to 10.0 wt. % of at least one substance with tissue growth activity, 0.01 to 5.0 wt. % lidocaine, 0.01 to 5.0 wt. % of at least one phenothiazine derivative, and 0.01 to 3.0 wt. % of at least one proteolytic enzyme, based on the total weight of the composition.

From the at least one additional agents, an antimicrobial substance is preferred. In the present invention, the antimicrobial substance is different from the cationic surfactant.

If at least one additional agent is employed in the method of the first aspect of the present invention, the method preferably comprises the following steps (a) to (c):

(a) providing the highly dispersed silica particles, the hydrophobic silica particles, the cationic surfactant and the at least one additional agent;

(b) forming primary hydrophobic silica particles carrying the cationic surfactant on their surface and/or agglomerates of these primary particles;

(b2) mixing a the highly dispersed silica particles with the at least one additional agent; and (c) mixing the products obtained in steps (b) and (b2).

If step (b2) is carried out, steps (b) and (b2) can be carried out sequentially in any order or concomitantly.

More preferably, the method comprises the following steps (a) to (c):

(a) providing the highly dispersed silica particles, the hydrophobic silica particles, the cationic surfactant and the at least one additional agent;

(b) forming primary hydrophobic silica particles carrying the cationic surfactant on their surface and/or agglomerates of these primary particles;

(b2) mixing a minor part of the highly dispersed silica particles with the at least one additional agent; and (c) mixing the major part of the highly dispersed silica particles with the products obtained in steps (b) and (b2).

Even more preferably, the method comprises the following steps (a) to (c):

(a) providing the highly dispersed silica particles, the hydrophobic silica particles, the cationic surfactant and the at least one additional agent;

(b) forming primary hydrophobic silica particles carrying the cationic surfactant on their surface and/or agglomerates of these primary particles;

(b2) forming primary highly dispersed silica particles carrying the at least one additional agent on their surface and/or agglomerates of these primary particles using a minor part of the highly dispersed silica particles; and (c) mixing the major part of the highly dispersed silica particles with the products obtained in steps (b) and (b2).

If in the above method, a minor part of the highly dispersed silica particles is employed in step (b2) and a major part of the highly dispersed silica particles is employed in step (c), the major part of the highly dispersed silica particles preferably represents 70 to 95 wt. %, more preferably 80 to 90 wt. %, most preferably 85 to 89 wt. % of the total weight of the highly dispersed silica comprised in the composition and the remaining highly dispersed silica particles form the minor part of the highly dispersed silica particles employed in step (b2).

In the method of the first aspect of the present invention, the formation of the primary particles or their agglomerates in step (b) is preferably achieved by mixing the respective components using a hermetically sealed high-speed mixer with vane.

More preferably, the formation of the primary particles or their agglomerates in steps (b) and (b2) is achieved by mixing the respective components using a hermetically sealed high-speed mixer with vane.

When step (b) and/or step (b2) are carried out by mixing the respective components, the method preferably further comprises the steps of:

(i) adding ethanol and/or water before or during mixing in an amount of 10 to 100 wt. % based on the weight of the highly dispersed silica or the hydrophobic silica, respectively; and (ii) drying the composition after mixing.

By adding ethanol and/or water in an amount of 10 to 100 wt. %, preferably 10 to 60 wt. %, most preferably 25 to 50 wt. % based on the weight based on the weight of the highly dispersed silica or the hydrophobic silica, respectively in step (b) and/or (b2), the formation of primary hydrophobic silica particles carrying the cationic surfactant on their surface and/or agglomerates of these primary particles, and/or the formation of primary highly dispersed silica particles carrying the at least one additional agent on their surface and/or agglomerates of these primary particles can be intensified. When in the present invention reference is made to the amount of "ethanol and/or water", either ethanol or water can be employed alone, which means that the amount refers to the amount of ethanol or water, respectively. If both of ethanol and water are employed in combination, the amount refers to the total amount of ethanol and water.

In the method of the first aspect of the present invention, the formation of the primary particles or their agglomerates in step (b) is most preferably achieved by milling the respective components. If, in this case, the method comprises the step (b2), the formation of the primary particles or their agglomerates in step (b2) can be achieved by mixing the respective components using a hermetically sealed high-speed mixer with vane. However, it is preferred that the formation of the primary particles or their agglomerates in step (b2) is also achieved by milling the respective components.

When step (b) and/or step (b2) are carried out by milling the respective components, the method preferably further comprises the steps of:

(i) adding ethanol and/or water before milling in an amount of 10 to 100 wt. % based on the weight of the highly dispersed silica or the hydrophobic silica, respectively; and (ii) drying the composition after milling.

By adding ethanol and/or water in an amount of 10 to 100 wt. %, preferably 10 to 60 wt. %, most preferably 25 to 50 wt. % based on the weight based on the weight of the highly dispersed silica or the hydrophobic silica, respectively in step (b) and/or step (b2), the formation of primary hydrophobic silica particles carrying the cationic surfactant on their surface and/or agglomerates of these primary particles, and/or the formation of primary highly dispersed silica particles carrying the at least one additional agent on their surface and/or agglomerates of these primary particles can be intensified.

In the method of the first aspect of the present invention, the formation of the primary particles or their agglomerates in steps (b) and (b2) is most preferably achieved by milling the respective components. Preferably, the milling is carried out using a ball mill or a vibrational mill. When a ball mill having a drum volume of 2 liters is used in step (b), preferably the time of milling is 30-60 minutes, and the speed of rotation of the drum is 0.5-2 rev/sec. When a ball mill having a drum volume of 2 liters is used in step (b2), preferably the time of milling is 20-60 minutes, and the speed of rotation of the drum is 0.5-2 rev/sec. For ball mills having a higher drum volume of, e.g., 5, 10, or 50 liters, the time of milling may be higher, e.g., 60 to 120 min. Thus, when a ball mill having a drum volume of 10 liters is used in step (b), preferably the time of milling is 30-90 minutes, and the speed of rotation of the drum is 0.5-2 rev/sec.

In the above described method, step (c) is preferably carried out using a hermetically sealed high-speed mixer with vane. The mixing time should preferably be sufficient to obtain a finely dispersed, visually homogeneous powder preparation. Preferably, the mixing time is 5 to 20 minutes, more preferably about 10 minutes.

In a preferred embodiment of the above described method according to the first aspect of the present invention the cationic surfactant is mechanochemically immobilized onto the hydrophobic silica particles in step (b). If the method comprises a step (b2), the at least one further substance is preferably also mechanochemically immobilized onto the highly dispersed silica particles in step (b2).

Mechanochemical immobilization (or mechanochemically initiated immobilization) is a process by which substances such as active ingredients are applied and/or attached (fixed) to the surface of a carrier material by mechanochemistry techniques.

According to the present invention, the term "mechanochemically immobilized" means that an active ingredient is present on the surface of the particles of a solid carrier material. The carrier material is one of the sorbents used in the present invention, i.e., hydrophobic silica particles or highly dispersed silica. E.g., a reference to "a cationic surfactant is mechanochemically immobilized onto hydrophobic silica particles" means that the surfactant (active ingredient) is present on the surface of the hydrophobic silica particles (solid carrier material). Similarly, a reference to "an antimicrobial substance is mechanochemically immobilized onto highly dispersed silica" means that the antimicrobial substance (active ingredient) is present on the surface of the highly dispersed silica particles (solid carrier material). Preferably, the active ingredient forms a molecular layer on the surface of the nanometer sized carrier material particles. Thereby, the total surface of the active ingredient is increased. Thus, the total quantity of active ingredient molecules which are ready to exercise their pharmacological activity in case of "mechanochemical immobilization" is higher than in a composition containing larger particles of the active ingredients.

The mechanochemical immobilization includes two aspects, i.e. (1) a mechanochemical process which is a physical chemical process or chemical reaction initiated by a mechanical process (beating, friction, ultra sonic and so on); and (2) the immobilization. Thus, the mechanochemical immobilization results in physical chemical fixing of the active ingredient on the surface of the carrier material particles with the help of a mechanical process in which impact forces and friction forces are exerted to the components which are mechanochemically immobilized onto each other.

The mechanochemical immobilization is carried out for a certain period of time which is necessary for even immobilization of the active ingredient on the carrier material particles. If the time of the process is too short the result may be a simple mixture of crushed particles of the ingredients.

In the above described method according to the first aspect of the present invention the minor part of the highly dispersed silica particles employed in step (b2) preferably represents 5 to 30 wt. %, more preferably 10 to 20 wt. %, most preferably 11 to 15 wt. % of the total weight of the highly dispersed silica comprised in the composition. Preferably, the remaining highly dispersed silica particles form the major part of the highly dispersed silica particles employed in step (c), which preferably represents 70 to 95 wt. %, more preferably 80 to 90 wt. %, most preferably 85 to 89 wt. % of the total weight of the highly dispersed silica comprised in the composition.

In step (b2) the mechanochemical immobilization of the antimicrobial substance onto the highly dispersed silica may be carried out using only a minor part of the highly dispersed silica since during the mechanochemical immobilization the highly dispersed silica is compressed whereby its sorption properties are reduced. Thus, the major part of the highly dispersed silica is not used in step (b2), but is mechanically mixed in step (c) with the mechanochemically immobilized products obtained in step (b).

In step (b2) the weight ratio of the weight of the antimicrobial substance to the weight of the highly dispersed silica is preferably in the range 2:1 to 1:4, more preferably 1.7:1 to 1:3, even more preferably 1.5:1 to 1:2 and most preferably 1.2:1 to 1:1.5. If the weight ratio is in the mentioned range, the surface of highly dispersed silica particles is large enough so that the antimicrobial substance can be fixed on the surface of the particles as a thin even layer of separate molecules which can easily be released to provide the antimicrobial action.

The process of mechanochemical immobilization can be carried out by any mill as long as it can provide mixing of the material and can exert impact forces and friction forces onto the material to be milled. Alternatively, a mixer, preferably a high-speed mixer with vane, can be employed. The advantage of using a ball mill is a rapid immobilization, while using a mixer, this process takes more time.

Exemplary mills suitable for carrying out mechanochemical immobilization are tumbling mills such as ball mills or rod mills; agitated ball mills, planetary mills, conus mills, centrifugal mills, VSI mills, jet-streamed mills, jet-mills, pin mills, vibrational mills, and a mixer with vane, i.e., a mixer with blades or paddles. Not suitable for carrying out mechanochemical immobilization is e.g. a hydraulic press because it cannot provide even allocation of the milled substances. Vibrational mills, centrifugal mills, jet-streamed mills and planetary mills are preferred due to their higher productivity. Preferably, the mechanochemical immobilization can be carried out using a ball mill or a vibrational mill. An exemplary ball mill having an internal volume of the drum of 2 to 10 liters is produced by the Ukrainian factory "SlavCeramicRefractory", Slavyansk (www.sko.com.ua/melnici-sharovye.html).

If a ball mill is used, the speed of rotation should be chosen so that the balls fall and/or tumble inside the mill drum. Thereby the balls can exert impact forces in addition to friction forces on the material which is milled. If the speed of rotation is too low, the balls will simply roll inside the mill and will not exert impact forces. The result may be a roughly blended mixture without even fixation of the active agents on the carrier material. If the speed is too high, the balls will be pressed to the wall of the drum by centrifugal forces so that neither impact forces nor friction forces are exerted.

More preferably, the mechanochemical immobilization can be carried out in ball mill using a porcelain drum having an internal volume of 2 liters at a speed of rotation of 1 rev/sec. i.e. 60 rpm, for a time of 20 to 60 min. For ball mills having a higher drum volume of, e.g., 5, 10, or 50 liters, the time of milling may be higher, e.g., 60 to 120 min. Thus, when a ball mill having a drum volume of 10 liters is used in step (b), preferably the time of milling is 30-90 minutes, and the speed of rotation of the drum is 0.5-2 rev/sec. If the duration of the milling is too long, the compression of the carrier material (highly dispersed silica or hydrophobic silica) is increased which may lead to a partial loss of its sorption qualities.

The composition of the present invention exhibits improved healing properties due to the "mechanochemical immobilization" of the active ingredients on the carrier material.

The fact that mechanochemical immobilization took place can be tested by way of X-ray powder diffraction, infrared spectroscopy and other kinds of analysis by means of diagrams before and after the processes.

In a second aspect, the present invention provides a composition in powder form comprising highly dispersed silica, hydrophobic silica and a cationic surfactant.

The composition of the second aspect of the present invention preferably comprises:
21.0 to 75.0 wt. % of highly dispersed silica,
16.0 to 70.0 wt. % of hydrophobic silica,
0.05 to 4.0 wt. % (preferably 0.1 to 4.0 wt. %) of the cationic surfactant,
based on the total weight of the composition.

More preferably, the composition of the second aspect of the present invention comprises:
35.0 to 70.0 wt. % of the highly dispersed silica,
20.0 to 45.0 wt. % of the hydrophobic silica, and
0.05 to 2.0 wt. % (preferably 0.8 to 2.0 wt. %) of the cationic surfactant,
based on the total weight of the composition.

With respect to the ratio of cationic surfactant and hydrophobic silica, the composition of the second aspect of the present invention preferably comprises:
90.0 to 99.8 wt. % of the hydrophobic silica, and
0.1 to 10 wt. % (preferably 0.2 to 10.0 wt. %) of the cationic surfactant,
based on the total weight of hydrophobic silica and cationic surfactant.

More preferably, the composition of the second aspect of the present invention preferably comprises:
95.0 to 99.0 wt. % of the hydrophobic silica, and
0.5 to 5.0 wt. % of the cationic surfactant,
based on the total weight of hydrophobic silica and cationic surfactant.

In the first and second aspects of the present invention, the sum of the highly dispersed silica and the hydrophobic silica represents 65 to 99.9 wt. %, preferably 90 to 99.5 wt. % of the total weight of the composition.

In a preferred embodiment of the second aspect, the present invention provides a composition in powder form comprising highly dispersed silica particles, hydrophobic silica particles, and a cationic surfactant, wherein at least 25% by weight, preferably 25 to 80% by weight, more preferably 40 to 80% by weight, most preferably 40 to 60% by weight of the cationic surfactant is present in primary hydrophobic silica particles carrying the cationic surfactant on their surface and/or in agglomerates of these primary particles.

In the present invention highly dispersed silica ($SiO_2$) is used, which is approved for clinical use as a medicine, as well as an excipient in many preparations [Blitz J. P. and Gun'ko V. M. (eds.) Surface Chemistry in Biomedical and Environmental Science, Springer, 2006, p. 191-204]. Highly dispersed silica is described in U.S. ("Silicon Dioxide"), British and European Pharmacopoeia ("Silica, Colloidal Anhydrous"). Highly dispersed silica in accordance with the present invention includes fumed silica, precipitated silica, colloidal anhydrous silica, silicagel, Syloid®, Aerosil®, or other types of porous or non-porous highly dispersed silica. Preferably, the highly dispersed silica is fumed silica, colloidal anhydrous silica, or silicagel. The highly dispersed silica is preferably comprised in the composition of the present invention in an amount of 21.0 to 75.0% by weight, preferably 35.0 to 70.0% by weight, based on the total weight of the composition. The particle size of the highly dispersed silica to be used in the present invention is preferably 2 to 200 nm, more preferably 4 to 150 nm, even more preferably 5 to 50 nm, most preferably 5 to 20 nm. Preferably, the particle size of the highly dispersed silica is not more than 100 nm. The water content of the highly dispersed silica to be used in the present invention is preferably no higher than 3 wt. %, more preferably no higher than 1 wt. %, most preferably less than 0.5 wt. %, based on the total weight of the highly dispersed silica.

Highly dispersed silica can be obtained by high temperature hydrolysis of silicone tetrachloride $SiCl_4$ according to the following reaction scheme:

$$SiCl_4 + 2H_2O \rightarrow SiO_2 + 4HCl$$

The product is usually characterized by a high chemical purity, i.e. the content of $SiO_2$ is not less than 99.9%. The surface area of highly dispersed silica depends on the conditions of synthesis and can range from 150 up to 380 $m^2/gm$.

For preparation of a medical sorbent such as the composition of the present invention, preferably fumed silica is used with a surface area of 300±30 $m^2/gm$.

In the fumed silica the primary spherical nonporous particles usually have a particle size 5 to 20 nm and may be represented by a 3D polymer $(SiO_2)_n$ where $n=10^4$–$10^5$ in which the atoms of silica and oxygen are linked by a siloxane bond ≡Si—O—Si≡ and the Si atoms show tetrahedral coordination, with 4 oxygen atoms surrounding a central Si atom. Due to hydrogen bonding, electrostatic and Van der Waals forces and with the help of adsorbed molecules of water the primary particles are united into aggregates having a size of about 100 to 200 nm which in turn form aggregates having a particle size of more than 1 μm.

The highly dispersed silica obtained by the above process is an amorphous solid, i.e. it does not have a crystal structure of long-range order. The surface of the highly dispersed silica is covered with hydroxyl groups as shown below, which define the properties of silica as an enterosorbent, i.e. high hydrophilicity, protein-sorption activity and the ability to adsorb microorganisms.

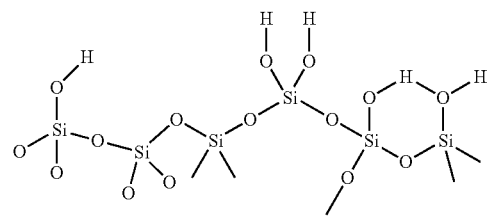

Nowadays the worldwide main producer of highly dispersed silica such as for medical application, is Evonik Industries. An exemplary highly dispersed silica, which can be employed in the first and second aspects of the present invention is Aerosil® 300 by Evonik Industries and A-300 by State Enterprise "Kalush Test Experimental Plant of Institute of Surface Chemistry of National Academy of Sciences of Ukraine".

In the first and second aspects of the present invention, the highly dispersed silica is preferably selected from the group consisting of fumed silica, precipitated silica, colloidal anhydrous silica, silicagel, Syloid®, Aerosil®, and combinations thereof.

In the present invention, the term "highly dispersed silica" refers to silica, which is hydrophilic by nature and readily wetted by water. Hydrophobic silica is not encompassed by the term "highly dispersed silica".

In contrast to highly dispersed silica, the hydrophobic silica is not wetted by water. Despite the higher density of these hydrophobic silicas in comparison with water, they float on the water surface. Therefore, the healing properties of hydrophobic silica itself are reduced. By forming primary hydrophobic silica particles carrying a cationic surfactant on their surface, the surface of the resulting surfactant covered hydrophobic silica particles becomes more hydrophilic and can provide better sorptive properties. This effect can be even more intensified by mechanochemical immobilization of a cationic surfactant onto the surface of hydrophobic silica particles, which can preferably be achieved by milling the components. The milling is preferably carried out using a ball mill.

In the present invention, the hydrophobic silica is preferably fumed hydrophobic silica or precipitated hydrophobic silica, more preferably fumed hydrophobic silica.

Preferably, the hydrophobic silica is highly dispersed silica having hydrophobic groups chemically bonded to its surface. More preferably, the hydrophobic silica is highly dispersed silica having alkyl or polydimethylsiloxane groups, preferably methyl groups, bonded to its surface. The hydrophobic silica is preferably obtainable by surface modification of highly dispersed silica using a surface treatment agent selected from the group consisting of dimethyldichlorosilane, octamethylcyclotetrasiloxane, polydimethylsiloxane, an organosilane, hexamethyldisilazane, an aminosilane, hexadecylsilane, methacrylsilane, silicone oil and combinations thereof, preferably dimethyldichlorosilane. The highly dispersed silica is preferably not surface modified by any of these agents.

In view of the surface modification, the hydrophobic silica preferably has a carbon content of 0.45 to 7.0 wt. %, preferably 0.5 to 4.0 wt. %, most preferably 0.6 to 2.0 wt. %.

The hydrophobicity of the hydrophobic silica can be characterized by the methanol wettability test. Preferably, the hydrophobic silica has a methanol wettability of 20 to 80 wt. %, more preferably 30 to 60 wt. %. On the other hand, the highly dispersed silica preferably has a methanol wettability of not more than 60 wt. %, more preferably not more than 5 wt. %.

The hydrophobic silica employed in the present invention has a very low density. In particular, the hydrophobic silica preferably has a tamped density of 30 to 250 g/L, preferably 40 to 150 g/L, most preferably 45 to 70 g/L. Furthermore, the hydrophobic silica has a high a BET surface area, which is preferably 15 to 300 m$^2$/g, more preferably 50 to 250 m$^2$/g, most preferably 70 to 250 m$^2$/g. In view of the high surface area, the hydrophobic silica can absorb high amounts of bodily fluids.

Fumed hydrophobic silica is commercially available from Evonik Industries under the trade name Aerosil®, such as Aerosil® R 972, R 972 Pharma, R 974, R 976, R 976 S, R 104, R 106, R 202, R 208, RY 300, RY 51, R 805, R 812, R 812 S, R 8200. RX 50, NAX 50, RX 200, RX 300, NX 90 S; NX 90 G, NX 130, R 504, RA 200 H, RA 200 HS, NA 50 H, R 816, R 709, R 711, R 7200, RY 50, NY 50, NY 50 L, RY 200, RY 200 L, RY 200 S, and NA 50 Y. Furthermore, precipitated hydrophobic silica is available from Evonik Industries as Sipemat® D 10 and D 17. In the present invention, preferably a hydrophilic silica selected from Aerosil® R 972, R 972 Pharma, R 974, and R 976 is employed, most preferably Aerosil® R 972 or R 972 Pharma.

Hydrophobic silica particles, such as Aerosil® R 972, in opposite to polymethylsiloxane (PMS) have an absolutely hydrophobic surface. As result, the hydrophobic silica particles are able to adsorb lipophilic substances (such as aminoacid tryptophan) from aqueous solutions.

The cationic surfactant used in the first and second aspects of the present invention is preferably selected from mono- or bis-quaternary ammonium compounds. More preferably, the cationic surfactant is selected from the group consisting of ethonium, decamethoxine, octenidine dihydrochloride, benzalkonium chloride, myramistine, and combinations thereof. Most preferably, the cationic surfactant is benzalkonium chloride. Benzalkonium chloride, also known as alkyldimethylbenzylammonium chloride, can be characterized by the following formula (I):

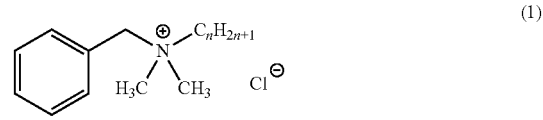

wherein n is between 5 and 24, preferably between 8 and 18, and more preferably n is selected from the group consisting of 8, 10, 12, 14, 16, and 18. Furthermore, benzalkonium chloride is preferably a mixture of alkylbenzyldimethylammonium chlorides of formula (1). An exemplary benzalkonium chloride is myristalkonium chloride (n=14).

Cationic surfactants in accordance with the present invention are mono-quaternary or bis-quaternary ammonium compounds or salts of primary and secondary amines. Preferably, the cationic surfactants are mono-quaternary or bis-quaternary ammonium compounds. In accordance with the present invention, a mono-quaternary ammonium compound is a compound having one quaternary ammonium group and a bis-quaternary ammonium compound is a compound having two quaternary ammonium groups. A quaternary ammonium group is a cationic group having 4 organic groups attached to a nitrogen atom. The salts of the quaternary ammonium compounds are preferably chlorides, bromides or iodides. When in the following a specific anion of a cationic surfactant is mentioned, this anion is considered to be a mere example of possible anions to be used with the respective cationic surfactant. Mono-quaternary or bis-quaternary ammonium compounds are known as preparations with high antimicrobial properties.

The cationic surfactant is preferably comprised in the composition of the present invention in an amount of 0.05 to 4.0% by weight, more preferably 0.05 to 4.0% by weight, more preferably 0.1 to 4.0% by weight, even more preferably 0.4 to 3.0% by weight, most preferably 0.8 to 2.0% by weight, based on the total weight of the composition. The composition of the present invention may comprise a single cationic surfactant or may comprise 2 or more different cationic surfactants.

Exemplary mono-quaternary ammonium compounds are benzalkonium chloride, benzethonium chloride, methylbenzethonium chloride, cetalkonium chloride, cetylpyridinium chloride, cetrimonium, cetrimide, didecyldimethylammonium chloride, myristamidopropyl-dimethylbenzammonium chloride (Myramistine®), dofanium chloride, tetraethylammonium bromide, and domiphen bromide. A particularly preferred mono-quaternary ammonium compound is benzalkonium chloride. Benzalkonium chloride is characterized by a wide spectrum of antimicrobial activity. It is used as an antiseptic, antifungal, antiprotozoal, preservative and spermicidal agent [Fleck C. A., "Palliative Dilemmas: Wound Odour". Wound Care Canada, 2006, vol. 4. No 3, p. 10-13].

Preferred bis-quaternary ammonium compounds are ethonium, and decamethoxine. Decamethoxine is most active against gram-positive bacteria, fungi and viruses [Moroz V. M., Paliy G. K., Sobolev V. O. and others. Comparison study of antimicrobial activity of antiseptics; News of Vinnitsa State Medical University, 2002, vol. 2, p. 315-320]. Established is its ability to activate the mononuclear phagocytic system cells. The spectrum of application of ethonium is similar to the spectrum of decamethoxine [Gridina T. L., Paliy G. K., Lositskiy V. P., Fedchuk A. S., "Results of the studies of different mechanisms of antiviral activity of decamethoxin and ethonium", Biomedical and Biosocial Anthropology, 2008; vol. 11, p. 43-45]. Octenidine dihydrochloride is a modern antiseptic with a great activity against MRSA [Hübner N. O., Siebert J., Kramer A., "Octenidine dihydrochloride, a modern antiseptic for skin, mucous membranes and wounds", Skin Pharmacol. Physiol., 2010, vol. 23(5), p. 244].

The molecules of the cationic surfactant, which is preferably benzalkonium chloride, interact with the hydrophobic silica surface by hydrophobic forces without forming covalent bonds and are realized by the attraction between methyl and methylene groups. As a result, the molecules of cationic surfactant cover the surface of the hydrophobic silica particles with a continuous layer. This attraction is intensified in an aqueous medium where the cationic surfactant acts as hydrophilizator.

A preferred secondary amine is octenidine dihydrochloride. It is similar in its antimicrobial action to the quaternary ammonium compounds, but is of somewhat broader spectrum of activity.

Besides their antimicrobial effect, cationic surfactants in the composition of the second aspect of the present invention act as detergents that hydrophilize the hydrophobic surface of hydrophobic silica particles, facilitating wetting of the hydrophobic surface of hydrophobic silica. Therefore, a problem of hydrophobic silica, that the exudate is not absorbed and spreads rapidly under the bandage which promotes skin maceration and activation of the inflammatory process in the wound, has been overcome. Furthermore, due to their effect of micellar catalysis, cationic surfactants significantly improve the activity of proteolytic enzymes (synergy effect).

The composition according to the second aspect of the present invention preferably further comprises at least one additional agent selected from the group consisting of antimicrobial substances, substances with tissue growth activity, lidocaine, phenothiazine derivatives, proteolytic enzymes, and combinations thereof.

More preferably, the composition of the second aspect comprises at least one of the following additional agents (in addition to the highly dispersed silica particles, the hydrophobic silica particles, and the cationic surfactant):
  0.5 to 10.0 wt. % of at least one antimicrobial substance,
  0.01 to 10.0 wt. % of at least one substance with tissue growth activity,
  0.01 to 5.0 wt. % lidocaine,
  0.01 to 5.0 wt. % of at least one phenothiazine derivative, and
  0.01 to 3.0 wt. % of at least one proteolytic enzyme,
  based on the total weight of the composition.

Even more preferably, the composition of the second aspect comprises:
  21.0 to 75.0 wt. % of the highly dispersed silica,
  16.0 to 70.0 wt. % of the hydrophobic silica, and
  0.05 to 4.0 wt. % (preferably 0.1 to 4.0 wt. %) of the cationic surfactant; and
  at least one of the following additional agents:
  0.5 to 10.0 wt. % of an antimicrobial substance,
  0.01 to 10.0 wt. % of at least one substance with tissue growth activity,
  0.01 to 5.0 wt. % lidocaine,
  0.01 to 5.0 wt. % of at least one phenothiazine derivative, and
  0.01 to 3.0 wt. % of at least one proteolytic enzyme,
  based on the total weight of the composition.

Most preferably, the composition of the second aspect comprises:
  35.0 to 70.0 wt. % of the highly dispersed silica,
  20.0 to 45.0 wt. % of the hydrophobic silica, and
  0.05 to 2.0 wt. % (preferably 0.8 to 2.0 wt. %) of the cationic surfactant, and
  at least one of the following additional agents:
  0.5 to 10.0 wt. % of an antimicrobial substance,
  0.01 to 10.0 wt. % of at least one substance with tissue growth activity,
  0.01 to 5.0 wt. % lidocaine,
  0.01 to 5.0 wt. % of at least one phenothiazine derivative, and
  0.01 to 3.0 wt. % of at least one proteolytic enzyme,
  based on the total weight of the composition.

In the above described method of producing a composition in powder form of the first aspect of the present invention and in the composition of the second aspect of the present invention, it is preferred that an antimicrobial substance is employed as the at least one additional agent.

An antimicrobial substance which can be used in the present invention is a compound which is capable of killing microorganisms or inhibiting their growth. For example, the antimicrobial compound may be active against bacteria, viruses, fungi, protozoa, and other microorganisms. The antimicrobial compound may be selective or non-selective for specific classes of microorganisms.

The antimicrobial substance is preferably comprised in the composition of the present invention in an amount of 0.5 to 10.0% by weight, preferably 1.5 to 8.0% by weight, based on the total weight of the composition. The antimicrobial substance used in the present invention may be a single substance or a mixture of two or more substances.

The antimicrobial substance may be selected from one or more compounds belonging to the following classes of compounds which include tetracyclines (e.g. minocycline), rifamycins (e.g. rifampicin), macrolides (e.g. erythromycin), penicillins (e.g. nafcillin), cephalosporins (e.g. cefazolin), other beta-lactam antibiotics (e.g. imipenem, aztreonam, carbacephems, carbapenems), aminoglycosides (e.g. gentamicin), chloramphenicol, sulfonamides (.e. sulfamethoxazole), glycopeptides (e.g. vancomycin), quinolones (e.g.

ciprofloxacin), fusidic acid, nitroimidazoles (e.g. metronidazole, tinidazole, nimorazole), thyazoles (e.g. nithazole), mupirocin, polyenes (e.g. amphotericin B), azoles (e.g. fluconazole), beta-lactamase inhibitors (e.g. sulbactam) and oxazolidinones (e.g. linezolid)). Beta-lactam antibiotics are preferably combined with a β-lactamase inhibitor such as clavulanic acid or their salts, sulbactam, or tazobactam. A particularly preferred combination is a composition comprising amoxicillin and potassium clavulanate.

The antimicrobial substance is preferably selected from one of the following substances: (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof.

Preferably, the antimicrobial substance used in the present invention does not encompass the above described cationic surfactants, i.e. cationic surfactants are preferably excluded from the meaning of the term "antimicrobial substance".

More preferably, the antimicrobial substances for use in the present invention are metronidazole, ciprofloxacin, fusidic acid, mupirocin, bacitracin, tyrothricin, metal-containing antimicrobials, compounds of boron or other substances with anti-anaerobic or anti-MRSA activity such as penicillin, amoxicillin, oxacillin, gentamycin, linezolid, erythromycin, clindamycin, moxifloxacin, co-trimoxazole, tetracycline, vancomycin, teicoplanin, rifampicin, phosphomycin, tigecycline, daptomycin.

Still more preferred antimicrobial substances for use in the present invention are metronidazole, ciprofloxacin, fusidic acid, mupirocin, bacitracin, tyrothricin, and compounds comprising silver and/or boron.

Preferred antimicrobial substances are metronidazole, ciprofloxacin, fusidic acid, mupirocin, bacitracin, tyrothricin, compounds of silver, compounds of boron or other substances with anti-anaerobic or anti-MRSA activity.

The spectrum of antimicrobial action of metronidazole (1-(β-hydroxyethyl)-3-methyl-5-nitroimidazole) includes simple organisms, anaerobic gram-negative bacteria, bacteroids (including *B. Fragilis*), fusobacteria, anaerobic gram-positive rods (including *Clostridium*), anaerobic gram-positive cocci (*Peplococcus, Peploslreptococcus*). Metronidazole is indicated for anaerobic infections of the skin and soft tissues, bones and joints in the treatment of wounds that do not heal for a long time [Gary R., Woo K. Y., "Local Wound Care for Malignant and Palliative Wounds", Advances in Skin & Wound Care: The Journal for Prevention and Healing, 2010, vol. 23, No 9, p. 417-428].

Ciprofloxacin is a representative of the fluoroquinolones that possesses a high level of activity against a majority of types of microorganisms, both gram-negative and gram-positive. Ciprofloxacin is used in drops and in ointments for local treatment of inflammatory diseases of eye and wounds [Donaldson P. M., Pallett A. P., Carroll M. P., "Ciprofloxacin in general practice", BMJ. (Clinical Research Ed.), May 1994, vol. 308, p. 1437].

Fusidic acid, baktroban (mupirocin), bacitracin, tyrothricin are also antimicrobial substances with high activity against MRSA.

Fusidic acid (chemical formula $C_{31}H_{48}O_6 \cdot 0.5H_2O$) has antibacterial, bacteriostatic effects and it inhibits bacterial protein synthesis. It is effective against *Staphylococcus* spp., including most strains of *S. aureus* (including MRSA) and *S. epidermidis* (including MRSE) and has activity against *Corynebacterium* spp., *Cladosporium* spp. [Lemaire S., Van Bambeke F., Pierard D., Appelbaum P. C., Tulkens P. M., "Activity of Fusidic Acid Against Extracellular and Intracellular *Staphylococcus aureus*: Influence of pH and Comparison With Linezolid and Clindamycin", CID, 2011, vol. 52 (Suppl. 7), p. 5493-503].

Mupirocin (baktroban) is an antimicrobial substance which inhibits bacterial protein synthesis. It is an effective bactericidal agent against infections caused by *Staphylococcus aureus*, including MRSA [Sutherland R., Boon R. J., Griffin K. E. et al., "Antibacterial Activity of Mupirocin (Pseudomonic Acid), a New Antibiotic for Topical Use", Antimicrobial Agents and Chemotherapy, 1985, vol. 27(4), p. 495-498].

Bacitracin is an antibiotic produced by strains of the bacteria *B. subtilis*, which is effective against a number of microorganisms. Typically it is used for external application in the treatment of diseases of the skin, eyes or nose, but it can also be administered orally, by injection, or as an intestinal antiseptic. In the food industry it is designated as E700 [European Pharmacopoeia 5.0, 2005, p. 1045-1047].

Tyrothricin is a cyclic polypeptide antibiotic derived from *Bacillus Brevis* that is topically effective against gram-positive bacteria. Tyrothricin contains gramicidin [Tyrosur® Gel-investigation on Wound Healing Efficacy (2010). Clinicaltrials.gov Identifier: NCT01227759. Latest update: Oct. 25, 2010. US National Institute of Health, US National Library of Medicine and US Department of Health & Human Services. Available from: http://clinicaltrials.gov/ct2/show/study/NCT01227759?term=tyrothricin].

Examples of metal-containing antimicrobials are silver, zinc, and copper, and their combined forms including salts, such as chloride, bromide, iodide, nitrate, sulphate, and periodate, complexes with carriers, and other forms.

Compounds comprising silver can be widely used in various medicinal forms for wound treatment, especially for burns. Exemplary compounds of silver are silver nitrate, colloidal silver, and nanosized silver.

Compounds of silver are preferably comprised in the composition of the present invention in an amount of up to 5.0% by weight, preferably 0.01 to 3.0% by weight, based on the total weight of the composition.

Examples of boron-containing antimicrobials for use in the present invention are alkali metal borate, alkaline earth metal borate, amine borate, boric acid and boric esters. Of these boron compounds, metal borates are preferred. These comprise sodium tetraborate, calcium silicate borate, sodium silicate borate, aluminum silicate borate, hydroboracite, aluminum borate, copper borate, magnesium borate, iron borate and zinc borate.

Boron-containing antimicrobials, such as sodium tetraborate, possess specific antibacterial activity against *Pseudomonas aeruginosa*. Another function of sodium tetraborate in some compositions is to turn the pH of the wound contents from acid values (which are caused by inflammation) to normal, i.e. not less than 7.0.

Compounds comprising boron are preferably comprised in the composition of the present invention in an amount of up to 5.0% by weight, preferably 0.01 to 3.0% by weight, based on the total weight of the composition.

In accordance with the present invention, substances with tissue growth activity are substances which can promote cell growth, whereby wound repair can be accelerated. Preferred examples of substances with tissue growth activity are compounds of zinc, methyluracil and growth factors such as epidermal growth factor (EGF), fibroblast growth factor (FGF, e.g. chicken embryo fibroblast-derived growth factor (CDGF)). More preferably, the substances with tissue growth activity are methyluracil and compounds of zinc.

Substances with tissue growth activity are preferably comprised in the composition of the present invention in an amount of up to 10.0% by weight, preferably 0.01 to 5.0% by weight, based on the total weight of the composition.

Compounds comprising zinc are involved in recovery processes in the later stages of wound healing, since zinc is an essential element in the biosynthesis of connective tissue. In addition, these compounds exhibit moderate antimicrobial activity [Bradley M. Cullum N., Nelson E. A. et al., "Systematic reviews of wound care management: (2) Dressings and topical agents used in the healing of chronic wounds", Health Technol. Assess., 1999, vol. 3 (17 Pt 2), p. 1-35]. Examples of zinc compounds include zinc oxide, zinc sulfate, and zinc hyaluronate. Methyluracil is well known for its tissue growth effect. Methyluracil stimulates the synthesis of nucleic acids and, thus, accelerates the generation of the cells.

Local anesthetics have immunological properties in addition to their direct anesthetic activity. Lidocaine inhibits adhesion, chemotaxis, phagocytosis, and the production of superoxide anion and hydrogen peroxide by neutrophils and macrophages. Local anesthetics may inhibit functions related to natural immunity in neutrophils and macrophages [Azuma Y., Ohura K., "Immunological modulation by lidocaine-epinephrine and prilocaine-felypressin on the functions related to natural immunity in neutrophils and macrophages", Current drug targets. Immune, endocrine and metabolic disorders, 2004, vol. 4(1), p. 29-36]. Lidocaine is included in the ointment <<Oflocaine-Darnytsia>>. Furthermore, lidocaine may be added to the composition of the present invention in the case of pronounced pain. Lidocaine can be comprised in the powder composition of the present invention in an amount of up to 5 wt. %, preferably up to 4 wt. %, more preferably 0.1 to 3 wt. % based on the total weight of the composition of the present invention. When in the present application reference is made to "lidocaine", pharmaceutically acceptable salts of lidocaine are included, in particular lidocaine hydrochloride.

Phenothiazines, herein also referred to as "phenothiazine derivatives", in accordance with the present invention are a class of neuroleptic antipsychotic drugs. A preferred phenothiazine to be used in the present invention is chlorpromazine. Phenothiazines such as chlorpromazine provide the composition of the present invention with unexpected stimulatory effects on the phagocytosis activity of wound macrophages [Cheplyaka O. M., "Complex therapy of patients suffering with anorectal abscess", Dissertation of PhD, Vinnitsa, 2006, p. 21]. Phenothiazines can be comprised in the powder composition of the present invention in an amount of up to 5 wt. %, preferably up to 3 wt. % based on the total weight of the composition of the present invention. Chlorpromazine can preferably be comprised in the powder composition of the present invention in an amount of up to 2 wt. %, more preferably up to 1.5 wt. % based on the total weight of the composition of the present invention.

Proteolytic enzymes in accordance with the present invention are enzymes that conduct proteolysis, i.e., which start protein catabolism by hydrolysis of the peptide bonds that link amino acids together in the polypeptide chain forming the protein. Examples of proteolytic enzymes include trypsin, chemotrypsin, terrylitin, microbial collagenase such as clostridial collagenase, and proteases derived from plants or fungi, such as papain, bromelaine and asperase.

Proteolytic enzymes may be added to the composition in case of treatment of wounds with a great amount of necrotic tissues which need to be decomposed before removal. In surgery enzymes with "soft" necrolytic activity such as trypsin and chemotrypsin and much stronger enzymes of microbial nature such as terrylitin and collagenase are utilized. Proteolytic enzymes can be comprised in the powder composition of the present invention in an amount of up to 3 wt. %, preferably up to 2 wt. % based on the total weight of the composition of the present invention.

It is preferred that the composition of the second aspect does not contain polymethylsiloxane. Thus, it is also preferred that no polymethylsiloxane is employed in the method of the first aspect of the present invention.

According to the present invention, polymethylsiloxane is a finely crushed hydrophobic powder having the general formula $(CH_3SiO_{1.5})_\infty$. Polymethylsiloxane is a xerogel of methylsilicic acid. Polymethylsiloxane is thus different from polydimethylsiloxane (PDMS).

In the second aspect of the present invention, the cationic surfactant is preferably mechanochemically immobilized onto the surface of the hydrophobic silica particles.

In a more preferred embodiment of the second aspect, the present invention provides a composition in powder form comprising highly dispersed silica particles, hydrophobic silica particles, and a cationic surfactant, wherein at least 25% by weight, preferably 25 to 80% by weight, more preferably 40 to 80% by weight, most preferably 40 to 60% by weight of the cationic surfactant is present in primary hydrophobic silica particles having the cationic surfactant mechanochemically immobilized onto their surface and/or in agglomerates of these primary particles.

The method of preparing the composition of the second aspect of the present invention is not particularly limited. However, it is particularly preferable, that the composition in powder form according to the second aspect of the present invention as described above is obtainable by the method of the first aspect of the present invention.

The particle size of the composition of the second aspect of the present invention is preferably 10 to 2,000 nm, more preferably 50 to 1,000 nm, even more preferably 100 to 500 nm. If the composition contains agglomerates, this particle size refers to the size of the primary particles which form the agglomerates. The size of the agglomerates can be in the range of from 2 μm to 500 μm, preferably 5 μm to 250 μm, more preferably 20 to 100 μm. In accordance with the present invention, an agglomerate is a cluster of primary particles held together by weak physical interactions.

The total water content of the composition of the present invention is preferably no higher than 3 wt. %, more preferably no higher than wt. %, most preferably less than 0.5 wt. %, based on the total weight of the composition.

The composition of the present invention is in the form of a powder. The sorbents highly dispersed silica and hydrophobic silica with a total content of approximately 90 wt. %, preferably represent 65 to 99.9 wt. %, more preferably 90 to 99.5 wt. % of the total weight of the composition, form the powder basis of the composition. The highly dispersed silica particles, hydrophobic silica particles, and a cationic surfactant are the ingredients of the composition which are always present, while other ingredients (i.e., antimicrobial substances, substances with tissue growth activity, lidocaine, phenothiazine derivatives, and proteolytic enzymes) may be added to the basis if needed. Consequently, compositions with a wide range of contents can be prepared depending on the purpose of the treatment. Additionally, depending on the purpose of the treatment different liquid and soft forms may be obtained (suspension, gel, ointment, drops and other) by dispensing the powder composition in a relevant medium. Tablets may be obtained by mixing the composition with excipients and pressing it. Finally, it is possible to include the composition in any aforementioned form in various medicinal articles (dressings, packets, capsules and others) for internal or external use.

The effectiveness of the composition of the present invention for the treatment of wounds is largely due to its sorption properties. Large wounds produce a significant amount of fluid. The removal of exudate from the wound surface is necessary to prevent the reabsorption of toxic breakdown products of necrotic tissues into the body.

Necrolytic properties, along with dehydrative, sorptive and antimicrobial activity make the composition of the present invention a "preparation of choice" for the local treatment of purulent wounds. This applies especially in the case of purulent wounds at anorectal abscesses which are complicated by putrid infection. The use of the composition to accelerate the rejection and breakdown of necrotic tissue allows to avoid necrectomy during repeated surgical interventions and reduces the number of medical manipulations, including dressings.

The high adhesion of the composition to necrotic tissue is particularly important in the treatment of purulent lesion areas in which it is difficult to conduct adequate sanitation by conventional surgical techniques due to the nature of the anatomical location and size of the purulent focus and the duration of the inflammatory process. When retroperitoneal phlegmon is present on a background of pancreatic necrosis using the composition can reduce the duration of drainage by 1.8 times. The use of this composition to accelerate the rejection and lysis of necrotic tissue allows for thorough regular necrectomy in a purulent focus. Thus, due to fragmentation and enhancement of the fluidity of the purulent exudates removal of the lysed tissue via drainages is simplified.

Combined lesion of a limb in a mixed form of the diabetic foot syndrome causes features of a disease, which lead to a weakening of the delimitation mechanisms of the purulent necrotic process, which explains the very high risk of amputation in these patients. The mixed form of diabetic foot syndrome is characterized by protracted infection, even in the case of successful correction of arterial insufficiency. This often manifests itself in a slowdown of the wound repair processes, recurrent necrotic lesions of bone and soft tissue and wound contamination by methicillin-resistant staphylococci. Clearance of purulent inflammation by the composition of the present invention allows to perform reconstructive plastic surgery with preservation of the support function of the foot.

Use of the composition in the surgical treatment of malignant tumors of the larynx, oropharynx and hypopharynx blocks the action of saliva, which shows lytic properties of tissues in the neck and contributes to the spread of the microflora from the oral cavity and pharynx, thereby increasing the duration of healing of postoperative wounds due to the frequent occurrence of wound complications—such as pharyngeal fistulas, skin flap necrosis, wound suppuration and, consequently, neck vessels arrosion—the internal jugular vein and carotid artery, with the emergence of profuse bleeding. The composition effectively cleans the wound from necrotic tissue, even in the case of radiation therapy and chemotherapy. Using the preparation eliminates the need for detoxification and systemic antibiotic therapy, even in cases of multipreparation-resistant wound microflora.

Use of the preparation allows to significantly reduce the quantity of infectious complications of pressure ulcers including bacteremia and sepsis, cellulitis, osteomyelitis, septic arthritis, and sinus tracts or abscesses.

The present invention also provides a pharmaceutical preparation which is or comprises the composition in powder form according to the second aspect of the present invention or the composition in powder form obtainable by any of the above described methods of preparing the composition of the first aspect of the present invention. Thus, the pharmaceutical preparation can be the composition in powder form according to the present invention, i.e., the pharmaceutical preparation can consist of the composition in powder form according to the second aspect of the present invention.

Alternatively, the pharmaceutical preparation may comprise in addition to the composition in powder form according to the second aspect of the present invention further additives. The pharmaceutical preparation is preferably in the form of a powder, a suspension, a gel, hydrogel, an ointment, drops, or a suppository, more preferably a powder or a suspension.

The pharmaceutical composition may also be present in the form of a hydrogel which comprises the composition in powder form according to the second aspect of the present invention in an amount of at least 2% by weight, preferably at least 5% by weight, most preferably at least 10% by weight based on the total weight of the preparation. The hydrogel can be prepared by mixing the composition in powder form according to the present invention with a hydrogel that is commonly used for wound treatment such as NU-GEL® (Johnson&Johnson), Prontosan Wound Gel® (B.Braun), Purilon Gel® (Coloplast), URGO® hydrogel (Urgo), Varihesive® Hydrogel (ConvaTec), Suprasorb® G Amorphes Gel (Lohmann&Rauscher), Askina® Gel (B.Braun), CURAFIL® (Tyco Healthcare), Hydrosorb® Gel (Hartmann), Cutimed® Gel (BSN medical), Intrasite Gel (Smith&Nephew), NOBAGEL® (NOBA), Normlgel® (Mölnlycke Health Care GmbH), Tegaderm™ Hydrogel (3M Medica) and any of commercial preparations of vitreous body (vitreous humor).

The present invention also provides a medical article selected from the group consisting of a dressing, packets, or capsules, comprising the pharmaceutical preparation of the present invention described above.

The composition or the pharmaceutical preparation of the present invention and, preferably, the composition according to the second aspect of the present invention can be used in the treatment of purulent wounds and necrotic wounds. More specifically, the composition or the pharmaceutical preparation can be used in the treatment of infected burn surfaces, putrid necrotizing phlegmons and noma in the maxillofacial region, wounds during a larynx or laryngopharynx resection after a cancer surgery, inflammatory diseases of the throat, mouth cavity and/or teeth, pharyngitis, tonsillitis, gingivitis and stomatitis, periodontitis, dental application and ultraphoresis, diseases of the rectum, the large intestine and organs of abdominal cavity, peritonitis, intra-abdominal and pancreatogenic abscesses, complications after pancreatonecrosis, extraperitoneal phlegmons, inflammatory diseases of the uterus and uterine adnexa, urinary bladder, pleura, bones, and other visceral organs, osteomyelitis, urethritis caused by gonococci, trichomonases and other infections, diseases in the front part of the eyes, a fistular in traumatic surgery, food intoxication, acute intestinal obstruction and intoxications by a virus, wounds and impetiginous diseases of the skin, acne, folliculitis and sycosis in the face and/or diseases provoked by irrational application of cosmetics, hemorrhoids, proctitis, anorectal abscesses, anal fissures, wounds after gynecological surgeries, non-specific trichomonal and fungal colpitis, vaginitis, vulvitis, metritis, parametritis, salpingitis, infectious diarrhea, infections caused by *Staphylococcus aureus*, methicillin-resistant *Staphylococcus aureus* (MRSA), multi-resistant gram-negative bacteria, enterobacteriaceae, and non-fermenting bacteria.

Moreover, the composition in powder form may be mixed in an amount of at least 2% by weight with an aqueous solution, preferably an aqueous solution containing sodium chloride, more preferably an isotonic sodium chloride solution, based on the total weight of the resulting aqueous composition. This aqueous composition is useful in the treatment of infections or inflammations of the urinary tract or the bladder.

The composition in powder of the second aspect of the present invention can be used for the local treatment of infected wounds. Furthermore, a suspension comprising 1 to 4 wt. % of the composition can be used perorally and for washing of body cavities such as gastric lavage; oral (in case of gingivitis, stomatitis, etc.) and nasal cavities; urine bladder (e.g., during pyuria and bacteriuria); uterus and vagina (e.g., during endomyometritis, bacterial vaginosis, for the prevention and treatment of purulent-resorptive complications after childbirth). The composition is also suitable for washing of the cavities of deep wounds and pathological processes, including abscesses of various localizations (lungs, liver, intra-abdominal, etc.), retroperitoneal phlegmon in pancreatic necrosis, deep cellulitis of the neck and mediastinitis, and pelvic anorectal abscess, etc. Furthermore the composition is useful for hemostasis during resection of parenchymal organs (liver, kidney, etc.).

This invention also relates to a method of producing the composition of the present invention which can be realized in two variants (conducted on at least two scales), namely in industrial scale (large scale) and pharmacy scale (small scale).

The industrial production of the composition includes
(a) providing highly dispersed silica particles, hydrophobic silica particles, and a cationic surfactant, and, optionally, an antimicrobial substance, and/or salts of zinc and/or methyluracil and/or lidocaine and/or chlorpromazine, and/or zinc oxide and/or proteolytic enzymes,
(b) mechanochemical immobilization of cationic surfactant onto the hydrophobic silica,
(b2) optionally mechanochemical immobilization of the antimicrobial substances and/or salts of zinc and/or methyluracil and/or lidocaine and/or chlorpromazine onto a minor part (5 to 30 wt. %, preferably 10 to 20 wt. %, more preferably 11 to 15 wt. % of the total weight of the highly dispersed silica comprised in the composition) of the highly dispersed silica, and
(c) mixing the major part (70 to 95 wt. %, preferably 80 to 90 wt. %, more preferably 85 to 89 wt. %) of the total weight of the highly dispersed silica comprised in the composition of the highly dispersed silica with the products obtained in steps (b) and (b2) and, if necessary, zinc oxide and/or proteolytic enzymes for a time sufficient to obtain finely dispersed, visually homogeneous powder composition. Steps (b) and (b2) can be carried out sequentially in any order or concomitantly.

The described pathway includes some novelties that allow to improve the therapeutical efficacy of the product. First of all, mechanochemical immobilization of a cationic surfactant onto the hydrophobic silica transforms it from hydrophobic to hydrophilic. Thus, the hydrophobic silica does not separate from the exudate and adheres to the wound surface. Then, due to mechanochemical immobilization of the active agents onto the silica particles, they can be better released and, as a result, the activity of the active agents is increased. Both of these properties were not evident and could not have been predicted on the basis of the known properties of cationic surfactants (antimicrobial) and of other active agents (antimicrobial, recovering, anesthetic, etc.).

A more simple way of obtaining the composition of the present invention ("pharmacy pathway") includes mechanical mixing of hydrophobic silica, highly dispersed silica, and a cationic surfactant, and, optionally further, at least one additional agent selected from the group consisting of antimicrobial substances, substances with tissue growth activity, lidocaine, phenothiazine derivatives, proteolytic enzymes, and combinations thereof at choice for a time sufficient to obtain a finely dispersed, visually homogeneous powder preparation.

According to a preferred embodiment of the present invention, the method includes (a) providing highly dispersed silica particles, hydrophobic silica particles, and benzalkonium chloride, (b) mechanochemical immobilization of benzalkonium chloride onto the hydrophobic silica using a ball mill (time of mixing 45-90 minutes, speed of rotation of the drum 0.5-2 rev/sec) or another type of mill; and (c) mixing the highly dispersed silica with the product obtained in step (b) in a hermetically sealed high-speed mixer with vane, i.e. a mixer with blades or paddles, during a time sufficient to obtain a finely dispersed, visually homogeneous powder composition, e.g., 5 to 20 minutes, preferably about 10 minutes.

According to a first embodiment of the present invention the method includes (a) providing highly dispersed silica particles, hydrophobic silica particles, benzalkonium chloride, mupirocin and lidocaine, (b) mechanochemical immobilization of benzalkonium chloride onto the hydrophobic silica using a ball mill (time of mixing 30-60 minutes, speed of rotation of the drum 0.5-2 rev/sec) or another type of mill; (b2) mechanochemical immobilization of mupirocin and lidocaine onto a minor part of the highly dispersed silica using a ball mill (time of mixing 30-60 minutes, speed of rotation of the drum 0.5-2 rev/sec) or another type of mill; and (c) mixing the major part of highly dispersed silica with the products obtained in steps (b) and (b2) in a hermetically sealed high-speed mixer with vane during a time sufficient to obtain a finely dispersed, visually homogeneous powder composition.

In accordance with another embodiment of the present invention, the method includes mixing of hydrophobic silica, highly dispersed silica, decamethoxine, metronidazole and zinc oxide in a hermetically sealed high-speed mixer with vane during a time sufficient to obtain a finely dispersed, visually homogeneous powder. Ethanol or water in an amount of 10 to 60 wt. %, more preferably 25 to 50 wt. % based on the sum of the weight of the highly dispersed silica and the hydrophobic silica (i.e., the sorbents) may be added before or during mixing, followed by drying the composition after mixing.

The composition without involving its direct antimicrobial effects leads to a significant reduction of pathogenic properties of microorganisms due to its fast and firm absorption which therefore constitutes an important achievement of the present invention regarding the therapeutic action of the composition in the local treatment of purulent wounds.

Thus, considering the type of the infectious agent, the spectrum of antibacterial activity of the composition of the present invention can be modified in wide range by changing the type and amount of its ingredients.

Taking into consideration the multipurpose property of the proposed compositions to adsorb a large scale of microorganisms and toxins, it can be used for treatment not only of wounds but of a large scope of diseases which have infectional etiology.

Thus, embodiments of the present invention may be used for treating purulent-inflammatory diseases of soft tissues and visceral organs, as well as human and animals' infections by the following ways of applications:

application of a pharmaceutical preparation comprising the composition on the wound surface in one of the following forms—powder, gel, ointment, paste, and/or a bandage or absorption package comprising the composition;

washout and/or irrigation of visceral organs using the suspension form directly or with the help of drainage;

oral use of a pharmaceutical preparation comprising the composition in liquid form or in the form of a tablet;

rectal insertion of a pharmaceutical preparation comprising the composition in the form of suppositories and/or with the help of a probe and/or by means of insufflation;

intraurethral (through urethra) insertion of a suspension of the composition for healing urethritis provoked by gonococci, trichomonases and other infections.

The formulations and ways of application of the composition according to the present invention can be varied in a wide range.

For instance, in addition to the above described ways of usage, the powder may be used in combustiology for the treatment of infected burn surfaces, or in maxillofacial surgery for the treatment of putrid necrotizing phlegmons and noma in maxillofacial region.

The composition in the form of a powder can be used during a larynx or laryngopharynx resection after a cancer surgery when complications arise because saliva gets into the wound. Powder can be inserted rectally with the help of an insufflator with the aim of treating diseases of the rectum and the large intestine (colonosorption).

A pharmaceutical preparation of the present invention may be used as applique (vulnerosorption), for washing of cavities directly or through a drainpipe, orally (enterosorption), rectal in a kind of suppository, by insufflator or a drainpipe (colonosorption), and by delivery through containers to internal organs, and others.

A pharmaceutical preparation in the form of a suspension of the composition of the present invention in a concentration of 1-4 wt. % may be used for rinsing during an inflammatory disease of the throat, mouth cavity and/or teeth. The composition may be inserted by means of drainage, probe and/or any other means for the treatment of inflammatory diseases of the rectum and the large intestine, organs of abdominal cavity (for example, peritonitis, intraabdominal and pancreatogenic abscesses, complications after pancreatonecrosis, extraperitoneal phlegmons), inflammatory diseases of the uterus and uterine adnexa, urinary bladder, pleura, bones (osteomyelitis) and other visceral organs. In urological and venereal practice a suspension of the composition is inserted intraurethrally (through the urethra) to heal urethritis caused by gonococci, trichomonases and other infections. A pharmaceutical preparation comprising the composition may be used in the form of drops for the treatment of diseases in the front part of the eyes.

For instance, during surgical treatment of acute intestinal obstruction, adducent and abducent sections of the intestine may be washed out with a 1-4% suspension before getting clear scourage (rinsing waters). Before imposition of anastomosis in the adducent section of intestine, 150-300 ml of a 1-4% suspension of the composition may be inserted and left there.

Another way of usage is postsurgical wash-out by a suspension of the composition via drainage which is set intraoperatively. In traumatic surgery for the treatment of a fistular form of chronic osteomyelitis, a 1-4% suspension of the composition may be inserted into the external foramen of the fistular to achieve full elimination of inflammatory changes.

A suspension of the composition may also be used orally as an enterosorbent during treatment of food intoxication, acute intestinal obstruction and intoxications by any other etiology, for example, a virus. In the case of intoxication, the treatment is started with washing out of the stomach and intestine with a 1-3% suspension of the composition, whereafter it may be applied orally.

Soft forms of the pharmaceutical preparation (gel, ointment, etc.) with concentrations of the composition higher than in a suspension may be used for the local treatment of wounds and impetiginous diseases of the skin. In particular, for the treatment of acne a pharmaceutical preparation may be used as a 15% water gel of the composition. In ointment form the pharmaceutical preparation comprising the composition may be used for the treatment of folliculitis and sycosis in the face and/or diseases provoked by irrational application of cosmetics.

In proctology for the treatment of hemorrhoids, proctitis, anorectal abscess, or anal fissure the pharmaceutical preparation may used by rectal insertion of suppositories comprising the composition of the present invention.

Suppositories comprising the composition can also be inserted intravaginally for sanitation before and after surgery which may include gynecological surgeries, non-specific trichomonal and fungal colpitis, vaginitis, vulvitis, metritis, parametritis, salpingitis.

A pharmaceutical preparation comprising the composition in the form of a tablet and/or of an enterosorbent can be used for the treatment of pharyngitis, or tonsillitis, or as an orally disintegrating tablet for resolution in the mouth cavity in the case of gingivitis and stomatitis.

In the stomatology during local treatment of the parodentium, e.g. against periodontitis, forms of pastes of the pharmaceutical preparation which are prepared ex tempore by mixing the relevant substances such as antiseptic solutions, tincture and herbal extracts with the composition of the invention may be used. The derived pastes may be used for dental application and ultraphoresis.

The composition in the form of a powder and in other forms can be placed inside containers (capsules) for the delivery or prolongation of its shelf life. The composition can be incorporated into drainage bandages, plasters and other bandaging means.

The above mentioned forms of the pharmaceutical preparation may be produced ex tempore (suspension) as well as by factory production (suspension, gel, ointment, drops, tablets, containers, bandages and etc.) by adding the necessary relevant excipients.

For instance, in order to extemporaneously prepare a suspension of the powder composition, the composition may be dispersed in water or I.V. fluid for injection, until it is fully dispersed.

For obtaining an ointment, the powder composition may be dispersed in the ointment base, which is preferably hydrophilic (e.g. a mixture of PEGs with different molecular mass, proxanol, glycerin and others).

The gel form may be obtained by dispersing the powder composition in hydrogels of gelatin, collagen, starch, pectin, polyacrylic acid, polyacrylamide, polyvinylpyrrolidone, polyvinyl alcohol, alginate, derivatives of cellulose and other gel-forming polymers.

In order to obtain a tablet the powder composition may be mixed with microcrystalline cellulose, starch, polyvinylpyrrolidone and/or others additives before conducting granulation.

Suppositories may be obtained by evenly distributing the powder composition in the molten base, which includes cacao butter, alloys of glycerin and gelatin, paraffin and cacao butter or other combinations as additives, and if necessary emulsifiers.

Containers for delivery of the powder composition can be made from porous indissolvable or biodegradable materials (such as gelatin, derivatives from polylactic acid and other materials). For making surgical bandages the powder composition may be pressed into the woven material or filled in penetrable packages with the composition or by using techniques for the relevant process.

The composition of the present invention can be used in the local treatment of purulent and necrotic wounds. In modern surgery one of the most difficult tasks is the local treatment of soft tissues anaerobic infections and nonhealing wounds and ulcers in the conditions of impaired blood supply and innervation. Patients often have problems such as rapid destruction of tissues, slow cleaning of the wound, and generalization of infectious and inflammatory process (SIRS, sepsis). The reasons for these problems can be, e.g., a disorder of microcirculation (diabetic angiopathy, atherosclerosis), or immunosuppression (oncology, chemotherapy, radiation therapy, etc.).

In the first phase of wound healing commonly drugs are used that target suppression of infection in the wound, activation of the processes of rejection of necrotic tissues, and evacuation of the wound fluid together with the absorption of products of microbial and tissue decay.

The absorption of wound exudate, tissue and microbial decay products is one of the main goals of the treatment of wounds in the first phase of wound healing. Applicative sorption is a kind of absorption detoxification of the body, which accelerates healing by removing toxins from the wounds.

The advantages of compositions of the present invention which comprise nano-sized sorbents in the treatment of purulent wounds in the first phase of wound process are that they well register to the wound surface that proteins, microorganisms, and toxins are absorbed irreversibly; and that water is absorbed. Thus, the compositions of the present invention provide improved properties compared to ointments which may melt at the body temperature and flow down to the bottom of the wound cavity, which cannot absorb proteins and microorganisms, and which may be diluted by wound exudation.

The use of the composition of the present invention in the complex treatment of anorectal abscess patients, complicated by anaerobic infection and sepsis, allows to shorten the duration of the first phase of wound healing due to the rapid wound cleansing from necrotic tissues, diminishing of microbial contamination of the wound that reduces the duration of hospitalization and indexes of lethality.

In particular, the composition of the present invention can be used in the treatment of acute pelviorectal horseshoe-shaped extrasphincteric abscess, pelviorectal abscess, complicated by putrid infection, wounds after Crile's surgery, bedsore of sacral region, Carbuncle of interscapular region, wounds of calcaneal region, and diabetic foot syndrome.

Furthermore, the composition of the present invention can be used in the treatment of infectious diarrhea, where the sorbents can act as binders of the stool. The action of the composition in the treatment of diarrhea is mainly antibiotic due to the removal of germs and toxins. Thus, the composition can be used in the treatment carbapenem-resistant diarrhea.

The composition of the present invention can also be used in the treatment of infections caused by MRSA, such as pneumonia. A pneumonia can be treated by diluting the composition of the present invention in medical saline solution and inhaling the resulting preparation using a nebulizer.

The composition or the pharmaceutical preparation of the present invention can be used in the treatment of infections caused by *Staphylococcus aureus*, methicillin-resistant *Staphylococcus aureus* (MRSA), multi-resistant gram-negative bacteria, enterobacteriaccae (e.g., *Escherichia coli, Klebsiella pneumonia, Klebsiella oxytoca, Enterobacter cloacae, Proteus mirabilis, Morganella morganii, Serratia marcescens, Citrobacter freundii*), and non-fermenting bacteria (e.g., *Pseudomonas aeruginosa, Acinetobacter baumannii, pseudomonas*).

The term "powder", as used herein and unless defined otherwise, refers to a dry, bulk solid composed of a large number of very fine particles that may flow freely when shaken or tilted. The particle size of the powder is preferably 10 to 2,000 nm, more preferably 50 to 1,000 nm, even more preferably 100 to 500 nm.

In accordance with the present invention, the size of a particle is defined as the volume equivalent diameter of the particle, i.e., the diameter of a spherical particle having the same volume as the particle. The particles size can be measured by photon correlation spectroscopy (PCS). The PCS is a routine method of measuring particle sizes and their particle size distribution (PSD). Usually, there are no ideal powders with only one exact size of particles. Therefore, according to the present invention a specified particle size such as "100 nm" means the number average size of particles which can be derived from the PSD.

It is to be understood that the term "comprising", as used herein and unless defined otherwise, includes the meaning of "consisting essentially of" and the meaning of "consisting of". Accordingly, the term "comprising" may also be understood, in a narrower sense, as "consisting essentially of" or, in an even narrower sense, as "consisting of". The term "consisting essentially of" as used herein and unless defined otherwise, means that the composition can contain further components which do not affect the characteristics of the composition, wherein preferably, the further optional components are contained in an amount of not more than 10% by weight, preferably, not more than 5% by weight, more preferably, not more than 2% by weight, more preferably, not more than 1% by weight with respect to the total weight of the respective composition.

When in the present invention reference is made to a substance as a generic term, such as "cationic surfactant", and it is stated that this generic term "is selected from the group consisting of" a list of specified substances, such as "selected from the group consisting of ethonium, decamethoxine, octenidine dihydrochloride, benzalkonium chloride, myramistine, and combinations thereof", it is to be understood, that the composition of the present invention does not contain any other substances falling under the generic term, except those which are specifically mentioned.

It is to be understood that the term "major part", as used herein and unless defined otherwise, means "more than 50% by weight", preferably "at least 70% by weight". Similarly, the term "minor part", as used herein and unless defined otherwise, means "less than 50% by weight", preferably "not more than 70% by weight".

The present invention provides in a third aspect a method of producing a composition in powder form comprising the following steps:
(a) providing hydrophobic silica particles and a cationic surfactant; and
(b) forming primary hydrophobic silica particles carrying the cationic surfactant on their surface and/or in agglomerates of these primary particles,
thereby obtaining the composition in powder form.

In the method of the third aspect of the present invention, the composition obtainable from the method preferably comprises:
90.0 to 99.9 wt. % of the hydrophobic silica, and
0.1 to 10.0 wt. % of the cationic surfactant,
based on the total weight of the composition.

More preferably, the composition obtainable from the method of the third aspect of the present invention comprises:
90.0 to 99.8 wt. % of the hydrophobic silica, and
0.2 to 10.0 wt. % of the cationic surfactant,
based on the total weight of the composition.

Even more preferably, the composition obtainable from the method of the third aspect of the present invention comprises:
95.0 to 99.0 wt. % of the hydrophobic silica, and
0.5 to 5.0 wt. % of the cationic surfactant,
based on the total weight of the composition.

In the third aspect of the present invention, the step of forming primary hydrophobic silica particles carrying the cationic surfactant on their surface and/or in agglomerates of these primary particles are the same as in the first aspect of the present invention. Likewise, the hydrophobic silica and the cationic surfactant are the same as in the first and second aspects of the present invention. This applies to all preferred, more preferred, even more preferred, most preferred and particularly preferred embodiments of the first and second aspects of the present invention described above.

In particular, it is preferred that the formation of the primary particles or their agglomerates in step (b) is achieved by mixing the respective components using a hermetically sealed high-speed mixer with vane. Most preferably, the formation of the primary particles or their agglomerates in step (b) is achieved by milling the respective components. In either case, wherein step (b) preferably further comprises the steps of
(i) adding ethanol and/or water before milling in an amount of 10 to 100 wt. % based on the weight of the hydrophobic silica, respectively; and
(ii) drying the composition after milling.

In a preferred embodiment of the above described method according to the third aspect of the present invention the cationic surfactant is mechanochemically immobilized onto the hydrophobic silica particles in step (b). Mechanochemical immobilization can be achieved by the methods described above with respect to the first aspect of the present invention.

In a fourth aspect the present invention provides a composition in powder form obtainable by the method according to the third aspect. The composition in powder form obtainable by the method according to the third aspect corresponds to the product obtained in step (b) of the method according to the first aspect of the present invention.

It is obvious that the present invention is not limited to the above preferred embodiments and various alterations and modifications will become aware to the skilled person.

EXAMPLES

In the examples the following substances have been employed.

Hydrophobic silica supplied as a batch product by Evonik Company with the trade mark Aerosil® R 972 Pharma. Highly dispersed silica supplied as a batch product by Evonik Company with the trade mark Aerosil® 300. As a cationic surfactant benzalkonium chloride is used according to the European Pharmacopoeia, 9$^{th}$ edition. Gelatin was obtained from Aldrich.

To prepare the composition comprising hydrophobic silica, highly dispersed silica and benzalkonium chloride as a cationic surfactant, the following main equipment was involved:
a ball mill (SlavCeramic Ltd, Slavyansk, Ukraine) with a drum volume of 10 L with porcelain
cylinders as milling elements which filled ⅓ of the drum volume,
a high speed mixer with vane (4 L volume), and
a drying oven with a maximum temperature of 200-250° C.

Besides, routine small laboratory equipment was used, among them an open electronic scale to 200 g, funnels, spoons, beakers, cylinders, etc. The other materials also needed for the manufacturing process were: distilled water (supplied in bottles), ethanol 96% (European Pharmacopoeia, 9th edition), plastic bulk containers (3 L-5 L volume) for final product storage, and liquid means for disinfection of tools (preferably containing benzalkonium chloride).

Degree of Hydrophobicity (Methanol Wettability)

The degree of hydrophobicity is determined by titration. 0.2 g of the sample are weighed out into a 250 ml separating funnel and 50 ml of ultrapure water are added. The silica remains on the surface. Methanol is then added ml by ml from a burette. During addition, the separating funnel is shaken with a circular hand motion in such a manner that no vortices are formed in the liquid. Methanol is added in this manner until the powder is wetted. Wetting is recognized by all the powder sinking below the water surface. The quantity of methanol consumed is converted into wt. % of methanol and stated as the value for methanol wettability.

Carbon Content of Hydrophobic Silica

The carbon content of a sample of hydrophobic silica is obtained in accordance with ISO 3262-20 (chapter 8) by oxidation of the carbon in the sample through combustion in oxygen (purity 99.9% or higher) and the resulting $CO_2$ is measured by infrared (IR) detectors (e.g. Carbon Determination System, C632 by LECO).

BET Specific Surface Area

The BET specific surface area is determined according to ISO 9277 by measuring the amount of physically adsorbed gas according to the method of Brunauer, Emmett and Teller (BET method). The resulting surface area is a multipoint BET value and is expressed in $m^2/g$.

Tamped Density

The tamped density is measured in accordance with ISO 787-11 as follows:
A sample is taken from the bottom of the sample bottle with a spoon. Using a funnel, the powder is put into a tared cylinder, filling it to the 200-250 ml level, making sure there are no cavities and the surface is horizontal. The total weight of the cylinder is measured to a precision of 0.1 g. The cylinder is placed in a Tap-Pak volumeter, which is set for 1250 taps, and the apparatus is started. The volume of the tapped silica is measured to a precision of 1 mL when the apparatus stops. The tamped density is calculated by the following equation:

Tamped density [g/L]=(weight of sample [g])×1000/ (volume of sample [ml])

Production Example

In step 1, 150-200 g of Aerosil 300 were heated in an oven at 180° C. for 30 min for sterilization. After cooling, the Aerosil 300 is placed into a sterile plastic bulk container, and closed hermetically.

In step 2, the porcelain drum of the ball mill and milling elements were disinfected with ethanol 96%, then washed with distilled water and dried. Thereafter, 4.28 g of benzalkonium chloride were dissolved in 20-30 ml of ethanol 96%. 150 g of Aerosil R 972 Pharma were placed into the drum and the obtained benzalkonium chloride solution in ethanol was added. Then, the drum of the ball mill was closed and the content was mixed at a speed of 1 rev/sec for 60 min. The obtained powder was dried on a flat surface at temperature 30-40° C. The obtained semi-product was placed into a sterile plastic bulk container, and closed hermetically.

In step 3, the high speed mixer was disinfected with ethanol 96%, then washed with distilled water, and dried. 100 g of sterilized Aerosil 300 obtained in step 1 and 56.25 g of the semi-product obtained in step 2 were placed in a hermetically sealed high-speed mixer with a vane and stirred for 10 minutes. A composition in powder form was obtained (Product P). The amounts of the ingredients of the composition are given in Table 1.

The hydrophobic silica Aerosil R 972 Pharma employed in the Production Example exhibits a methanol wettability of about 40 to 50 wt. %, a carbon content of 0.6 to 1.2 wt. %, a BET specific surface area of 90 to 130 m$^2$/g, and a tamped density of about 50 g/L.

TABLE 1

Amounts of the ingredients of the composition of the Production Example

| Substance | Amount (wt. %) | Document | Trade mark | Supplier |
|---|---|---|---|---|
| Highly dispersed silica | 64 | European Pharmacopoeia | Aerosil 300 | Evonik |
| Hydrophobic silica | 35 | European Pharmacopoeia | Aerosil R 972 Pharma | Evonik |
| Benzalkonium chloride | 1 | European Pharmacopoeia USP/NF | — | Sigma-Aldrich |

Test Example: Adsorption of Gelatin 25.0 ml of a freshly prepared solution of 0.3 g of gelatin in 50 ml of water were added to 0.200 g of Product P in a 100 ml ground-glass-stoppered conical flask. The solution is shaken thoroughly for 1 h, afterwards centrifuged for 20 min and the supernatant liquid was filtered through a paper filter. 5.0 ml of the filtrate were diluted to 25.0 ml with biuret reagent. A reference solution was prepared by diluting 5.0 ml of a solution of gelatin (see above) to 25.0 ml with biuret reagent. After 30 min the absorbances (European Pharmacopoeia, 9$^{th}$ edition, 2.2.2) of the 2 solutions at 540-560 nm compared to a blank solution were measured using Specord M40, Carl Zeiss, Jena, Germany. To prepare a blank solution 5.0 ml of water were diluted to 25.0 ml with the biuret reagent.

The quantity of gelatin adsorbed per 1 g of preparation can be calculated from the following expression:

$$\frac{(A_0 - A) \cdot a \cdot 25}{A_0 \cdot m}$$

wherein $A_0$—absorbance of the reference solution; A—absorbance of the examined solution; a—mass in milligrams of gelatin in 1 ml of the solution of gelatin; m—mass in grams of the preparation which was examined.

Not less than 140 mg of gelatin was adsorbed per 1 g of Product P. Therefore, the composition according to Table 1 is suitable as a Wound Care Powder.

The invention claimed is:

1. A method of producing a composition in powder form comprising the following steps (a) to (c):
    (a) providing highly dispersed silica particles, hydrophobic silica particles, and a cationic surfactant;
    (b) forming primary hydrophobic silica particles carrying the cationic surfactant on their surface and/or agglomerates of these primary particles; and
    (c) mixing the highly dispersed silica particles with the product obtained in step (b), thereby obtaining the composition in powder form.

2. The method according to claim 1, wherein the cationic surfactant is selected from the group consisting of ethonium, decamethoxine, octenidine dihydrochloride, benzalkonium chloride, benzethonium chloride, myramistine, and combinations thereof.

3. The method according to claim 1, wherein the composition further comprises at least one additional agent selected from the group consisting of antimicrobial substances, substances with tissue growth activity, lidocaine, phenothiazine derivatives, proteolytic enzymes, and combinations thereof.

4. The method according to claim 1, wherein the composition comprises an antimicrobial substance selected from the group consisting of (a) metronidazole, (b) a fluoroquinolone, such as ciprofloxacine, (c) fusidic acid, (d) mupirocin, (e) bacitracin, (f) tyrothricin, (g) compounds of silver, (h) compounds of boron, and combinations thereof.

5. The method according to claim 1, wherein the formation of the primary particles or their agglomerates in step (b) is achieved by mixing the respective components using a hermetically sealed high-speed mixer with vane.

6. The method according to claim 1, wherein the formation of the primary particles or their agglomerates in step (b) is achieved by milling the respective components.

7. The method according to claim 6, wherein step (b) further comprises the steps of:
    (i) adding ethanol and/or water before milling in an amount of 10 to 100 wt. % based on the weight of the highly dispersed silica or the hydrophobic silica, respectively; and
    (ii) drying the composition after milling.

8. The method according to claim 6, wherein the milling is carried out using a ball mill or a vibrational mill.

9. The method according to claim 1, wherein step (c) is carried out using a hermetically sealed high-speed mixer with vane.

10. A composition in powder form comprising highly dispersed silica, hydrophobic silica and a cationic surfactant, wherein at least 25% by weight of the cationic surfactant is present in primary hydrophobic silica particles carrying the cationic surfactant on their surface and/or in agglomerates of these primary particles, and wherein the composition contains no polymethylsiloxane.

11. The composition according to claim 10, wherein the composition comprises
21.0 to 75.0 wt. % of highly dispersed silica,
16.0 to 70.0 wt. % of hydrophobic silica,
0.1 to 4.0 wt. % of the cationic surfactant,
based on the total weight of the composition.

12. The composition according to claim 10, wherein the sum of the highly dispersed silica and the hydrophobic silica represents 65 to 99.9 wt. %, preferably 90 to 99.5 wt. % of the total weight of the composition.

13. The composition according to claim 10, wherein the highly dispersed silica is selected from the group consisting of fumed silica, precipitated silica, colloidal anhydrous silica, silicagel, and combinations thereof.

14. The composition according to claim 10, wherein the hydrophobic silica is hydrophobic fumed silica, hydrophobic colloidal silica, or hydrophobic precipitated silica.

15. The composition according to claim 10, wherein the cationic surfactant is selected from mono- or bis-quaternary ammonium compounds.

16. The composition according to claim 10, further comprising at least one additional agent selected from the group consisting of antimicrobial substances, substances with tissue growth activity, lidocaine, phenothiazine derivatives, proteolytic enzymes, and combinations thereof.

17. A composition obtained by the method according to claim 1.

18. An aqueous composition which comprises the composition according to claim 10 in an amount of at least 2% by weight based on the total weight of the composition.

19. A medical article selected from the group consisting of a dressing, packets, or capsules, comprising the composition according to claim 10.

20. A method of treating purulent and necrotic wounds comprising using the composition according to claim 10.

21. A method of treating chronic inflammation of the urinary tract or bladder comprising using the aqueous solution of claim 18.

22. The composition according to claim 10, wherein the cationic surfactant is mechanochemically immobilized onto the surface of the primary hydrophobic silica particles.

* * * * *